US012605335B2

(12) United States Patent
Wu et al.

(10) Patent No.: US 12,605,335 B2
(45) Date of Patent: Apr. 21, 2026

(54) TRIPTOLIDE LIGNOCERATE, LIPOSOME THEREOF AND PREPARATION METHOD THEREFOR

(71) Applicants: SHANGHAI WEI ER BIOPHARMACEUTICAL TECHNOLOGY CO., LTD., Shanghai (CN); SHANGHAI BAOLONG PHARMACEUTICAL CO., LTD., Shanghai (CN); BAOLONG PHARMACEUTICAL CO., LTD., Anhui (CN); SHANGHAI BAOLONG ANQING PHARMACEUTICAL CO., LTD., Anhui (CN)

(72) Inventors: Xin Wu, Shanghai (CN); Hang Chen, Shanghai (CN); Xinmei Chen, Shanghai (CN); Jianming Chen, Shanghai (CN); Yongjie Huang, Shanghai (CN); Wuhao Wei, Shanghai (CN); Xinyu Wang, Shanghai (CN); Mengmeng Liu, Shanghai (CN)

(73) Assignees: SHANGHAI WEI ER BIOPHARMACEUTICAL TECHNOLOGY CO., LTD., Shanghai (CN); SHANGHAI BAOLONG PHARMACEUTICAL CO., LTD., Shanghai (CN); BAOLONG PHARMACEUTICAL CO., LTD., Anhui (CN); SHANGHAI BAOLONG ANQING PHARMACEUTICAL CO., LTD., Anhui (CN)

( * ) Notice: Subject to any disclaimer, the term of this patent is extended or adjusted under 35 U.S.C. 154(b) by 0 days.

(21) Appl. No.: 18/864,569

(22) PCT Filed: May 16, 2023

(86) PCT No.: PCT/CN2023/094423

§ 371 (c)(1),
(2) Date: Nov. 11, 2024

(87) PCT Pub. No.: WO2023/221961

PCT Pub. Date: Nov. 23, 2023

(65) Prior Publication Data

US 2025/0255813 A1 Aug. 14, 2025

(30) Foreign Application Priority Data

May 20, 2022 (CN) ......................... 202210549850.1

(51) Int. Cl.
*A61K 9/1271* (2025.01)
*A61K 9/00* (2006.01)
(Continued)

(52) U.S. Cl.
CPC .......... *A61K 9/1271* (2013.01); *A61K 9/0019* (2013.01); *A61K 9/1277* (2013.01);
(Continued)

(58) Field of Classification Search
None
See application file for complete search history.

(56) References Cited

U.S. PATENT DOCUMENTS

2003/0202997 A1* 10/2003 Campbell ............... A61P 33/14 514/552
2009/0252785 A1* 10/2009 Pollock .................. A61K 9/127 514/23

(Continued)

FOREIGN PATENT DOCUMENTS

| | | | | |
|---|---|---|---|---|
| CN | 1377282 A | | 10/2002 | |
| CN | 105853403 A | | 8/2016 | |
| CN | 106946975 A | * | 7/2017 | ............. A61K 47/26 |

OTHER PUBLICATIONS

Huang ZY. Studying the effects of fatty acid chain length on the properties of triptolide prodrugs in liposomes.2020. (Year: 2020).*

(Continued)

*Primary Examiner* — Isaac Shomer
(74) *Attorney, Agent, or Firm* — Liangang Ye

(57) ABSTRACT

The present invention relates to the technical field of pharmaceutics, and in particular to a triptolide lignocerate, a liposome thereof and a preparation method therefor. The chemical structural formula of the triptolide lignocerate is represented by formula (I). The triptolide lignocerate provided by the present invention is obtained by esterification of triptolide C14-OH and lignoceric acid. The anti-tumor effectiveness, safety and the like of the triptolide lignocerate liposome are further improved with respect to the prior art, (Continued)

so that a foundation is laid for providing safer and more effective triptolide-related clinical preparations.

Formula (I)

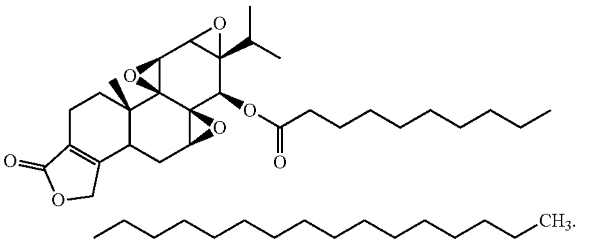

22 Claims, 3 Drawing Sheets

(51) Int. Cl.

| | |
|---|---|
| ***A61K 9/1277*** | (2025.01) |
| ***A61K 9/19*** | (2006.01) |
| ***A61K 31/585*** | (2006.01) |
| ***C07J 73/00*** | (2006.01) |
| ***C07J 75/00*** | (2006.01) |

(52) U.S. Cl.

CPC .............. *A61K 9/19* (2013.01); *A61K 31/585* (2013.01); *C07J 73/003* (2013.01); *C07J 75/00* (2013.01)

(56) References Cited

U.S. PATENT DOCUMENTS

| | | | | |
|---|---|---|---|---|
| 2016/0346205 | A1* | 12/2016 | Heath .................... | A61K 31/65 |
| 2019/0076357 | A1 | 3/2019 | Shan et al. | |

OTHER PUBLICATIONS

English Translation of CN 106946975 A. Originally published in Chinese on Jul. 14, 2017, translation obtained by examiner on Aug. 15, 2025, pp. 1-21. (Year: 2017).*

Aug. 30, 2023 International Search Report issued in International Patent Application No. PCT/CN2023/094423.

Aug. 30, 2023 Written Opinion of the International Searching Authority issued in International Patent Application No. PCT/CN2023/094423.

Liu Q. Triptolide and its expanding multiple pharmacological functions. International Immunopharmacology,2011,11 (3):377-383.

Noel Pvon Hoff DD, Saluja AK, et al. Triptolide and its derivatives as cancer therapies. Trends Pharmacol Sci,2019,40(5):327-341.

Song Yi, Liu Yan, Fang Bingqian, Kang Di, Hu Lihong. Research progress on the antitumor effect of triptolide and its mechanism of toxicity reduction[J]. Journal of Nanjing University of Traditional Chinese Medicine, 2021,37 (03):457-464.

Kitzen J J, de Jonge M J, Lamers C H, et al. Phase I dose-escalation study of F60008, a novel apoptsis inducer, in patients with advanced solid tumors. European Journal of Cancer, 2009, 45(10):1764-1772.

Tenchov R, Bird R, Curtze AE. Lipid Nanoparticles-From Liposomes to mRNA Vaccine Delivery, a Landscape of Research Diversity and Advancement. published online ahead of print. ACS Nano. 2021.

Wei Hong. Establishment and application of GC-MS method for the determination of plasma very long-chain fatty acids. Journal of Clinical Pediatrics, 2005(08):25-28.

* cited by examiner

TRIPTOLIDE LIGNOCERATE, LIPOSOME THEREOF AND PREPARATION METHOD THEREFOR

The present application is a National Stage of International Application No. PCT/CN2023/094423, filed on May 16, 2023, which claims priority of the Chinese Patent Application No. CN202210549850.1 filed on May 20, 2022.

TECHNICAL FIELD

The present invention is related to the field of pharmaceutical technology, specifically, the use of triptolide lignocerate and a liposome thereof and a preparation method therefor.

BACKGROUND

Triptolide (TP), also known as triptolide and triptolide alcohol, is an epoxy diterpene lactone isolated from the plant of the traditional Chinese medicine Tripterygium wilfordii Hook F. It has a wide range of pharmacological effects, including anti-inflammatory, immunosuppressive, antitumor, and antifungal effects. (Liu Q. Triptolide and its expanding multiple pharmacological functions[J]. International Immunopharmacology, 2011, 11(3):377-383). In the field of oncology, TP has been shown to have effective antitumor activity in a variety of cancers, and its antitumor effects have been widely studied. Additionally, TP has been shown to have good antitumor activity in nearly 60 tumor cell lines (NOEL PVON HOFF DD, SALUJA AK, et al. Triptolide and its derivatives as cancer therapies[J]. Trends Pharmacol Sci, 2019, 40(5):327-341), and it has the characteristics of a broad spectrum and high efficiency.

However, the starting dose at which TP exerts its activity is close to the toxic dose, resulting in a narrow therapeutic window (Song Yi, Liu Yan, Fang Bingqian, Kang Di, Hu Lihong. Research progress on the antitumor effect of triptolide and its mechanism of toxicity reduction[J]. Journal of Nanjing University of Traditional Chinese Medicine, 2021, 37(03):457-464.), there are also problems such as the short half-life and poor drug-forming properties of the preparation, which severely limit its application in the clinic. Therefore, an efficient drug targeting TP for antitumor therapy has not yet been developed and marketed. How to prolong the in vivo action time and reduce toxic side effects while maintaining the biological activity of TP is a key issue that needs to be solved to enable the safe and effective application of TP in the clinic.

A precursor drug is a new compound that is chemically bonded with a modifying group and can be enzymatically cleaved by the body's enzyme system to the parent drug to exert pharmacological effects. Precursor drug design is a common method used to change the physicochemical properties of antitumor drugs. The main purpose of this method is to improve digestion, absorption, distribution and metabolism (ADME), prolong the half-life, improve bioavailability, increase stability, reduce toxic side effects, and improve the in vivo pharmacokinetic properties of the parent drug to a certain extent. Owing to the water-insoluble nature of TP, most researchers are focused on structural modifications of TP and tend to design and synthesize new water-soluble TP derivatives with good pharmacokinetic properties to reduce the toxicity and side effects of drugs. For example, PG490-88Na, WilGraf, Minnelide, etc., are water-soluble prodrugs of TP (NOEL PVON HOFF DD, SALUJA AK, et al. Triptolide and its derivatives as cancer therapies[J]. Trends Pharmacol Sci, 2019, 40(5):327-341). Although the aforementioned prodrugs significantly increase the water solubility of TP by converting it into a salt, potential drawbacks such as rapid degradation and release or incomplete conversion have been observed. For example, in a phase I clinical dose-escalation study of PG490-88Na in patients with advanced solid tumors, intravenous injection was administered once a week with a one-week break every two weeks. The most frequently reported adverse reactions in the trial included anemia, malaise, nausea, vomiting, diarrhea, and constipation, all of which were graded from 1-2. In addition, pharmacokinetic studies have shown high interindividual variability (2- to 3-fold) in the pharmacokinetic properties of PG490-88Na, with unpredictable conversion to TP and a slow and incomplete conversion process.

PG490-88Na is not an ideal TP derivative, and a clinical trial has been forced to be suspended (Kitzen J J, de Jonge M J, Lamers C H, et al. Phase I dose-escalation study of F60008, a novel apoptsis inducer, in patients with advanced solid tumors [J]European Journal of Cancer, 2009, 45(10): 1764-1772). Minnelide is still in the phase II clinical study stage, and since then, there have been no relevant reports of its use in clinical trials. Whether the route by which TP salts improve water solubility can meet clinical needs is still debatable.

On the other hand, liposomes, as a hotspot of current research and development, have shown a wide range of application prospects, the advantages of which include the following: the toxicity can be reduced through the targeting effect at the same time to further improve the therapeutic efficacy; the drug wrapped in liposomes has an obvious slow and controlled release effect, greatly slowing the elimination rate of the drug in vivo and prolonging the half-life in vivo so that there is enough time for the drug to be targeted to the tumor site, reducing the distribution of the drug in normal tissues and thus improving the safety of clinical use. The above features are exactly the ideal effect that the TP urgently needs to achieve. With the development of formulation technology, many nanoformulations have been applied in the clinic, such as adriamycin liposomes (Doxi®), irinotecan liposomes (Onivyde™), cytarabine liposomes (Vyxeos®), and mRNA liposomes (Tenchov R, Bird R, Curtze A E. Lipid Nanoparticles—From Liposomes to mRNA Vaccine Delivery, a Landscape of Research Diversity and Advancement. published online ahead of print. ACS Nano. 2021). The above formulations fully illustrate the feasibility of the use of liposomes for the marketing of antitumor drugs, which can provide an important reference for the development of TP. However, owing to the poor solubility, short half-life, and poor drug-forming properties of TP itself, its direct preparation into liposomes has the problems of poor drug-forming properties, difficult preparation, and low encapsulation rates.

Therefore, the combination of lipid-soluble prodrugs and nanoformulations will be an important research tool to improve the drugability of insoluble drugs, improve their efficacy and reduce their toxicity. In Japan's Mitsubishi Pharmaceutical Co., dexamethasone palmitate fatty milk injection has been successfully developed and marketed, and the system of dexamethasone esterifies with palmitic acid to form a lipid-soluble prodrug, which is ultimately prepared for fatty milk injection, increasing its efficacy and reducing toxicity. Another example is the lauroyl aripiprazole extended-release injection developed by Alkermes, which was approved by the FDA in 2015. This method combines aripiprazole with fatty acids through a linkage group to obtain a strong fat-soluble derivative of aripiprazole, which is then prepared via extended-release injection, effectively prolonging the release of the drug and enhancing its therapeutic efficacy.

The Chinese patent document CN105853403A, which aims to solve the problem of poor drug formation of paclitaxel nanoformulation, disclosed a paclitaxel palmitate liposome and its preparation method. The patent esterified paclitaxel 2'-OH with saturated fatty acid to synthesize a series of paclitaxel fatty acid ester fat-soluble prodrugs, including paclitaxel myristate, paclitaxel palmitate, paclitaxel stearate, etc., and was separately prepared into liposomes, and the results of in vivo pharmacodynamic studies showed that among the many paclitaxel fat-soluble prodrugs, paclitaxel palmitate liposomes had the strongest antitumor effect. This may be because the longer fatty acid chain is, the longer the in vivo circulation time of paclitaxel predrugs, i.e., the slower the in vivo conversion to the parent drug paclitaxel, and the predrugs tend to be inactive or have low activity in vivo, and they can only play a role if they are converted to the parent drug. Therefore, the shorter chain of paclitaxel fatty acid esters (such as myristate) results in in vivo release of transformed paclitaxel too quickly to achieve sufficient long-circulation effects, and the longer chain of paclitaxel fatty acid esters (such as stearate) liposomes results in in vivo release of transformed paclitaxel too slowly to achieve the effective concentration of paclitaxel drug in vivo. In addition, among the many derivatives of paclitaxel fatty acid ester, paclitaxel palmitate in vivo long-circulation and, among the many derivatives of paclitaxel fatty acid esters, the speed of conversion and release of paclitaxel reaches an appropriate balance point so that the active parent drug paclitaxel can be released and converted to maintain a relatively high concentration for a long period of time in the body, i.e., the active parent drug in the body maximizes the time of circulation and the maintenance of the drug concentration, so that its antitumor effect is the strongest.

The Chinese patent document CN106946975A discloses a triptolide lipid-soluble derivative, which is obtained by esterifying eight saturated fatty acids, such as butyric, hexanoic, caprylic, decanoic, lauric, myristic, palmitic, and stearic acids, with triptolide C14-OH. The esterification modification greatly improved the druggability of triptolide, as the liposomal encapsulation rate of the eight triptolide lipid-soluble derivatives described above was greater than 90%, whereas the liposomal encapsulation rate of triptolide was less than 50%. In vivo pharmacokinetic studies revealed that the biological half-lives of triptolide released via the in vivo conversion of triptolide myristate liposomes, triptolide palmitate liposomes, and triptolide stearate liposomes were 80.4 min, 100.9 min, and 124.2 min, respectively, which greatly prolonged the half-life of triptolide ($t_{1/2}$=15 min), laying the foundation for a better antitumor effect in vivo.

In the literature (Huang Z Y. Studying the effects of fatty acid chain length on the properties of triptolide prodrugs in liposomes [D]. 2020), six lipid-soluble derivatives of triptolide fatty acid esters, including triptolide myristate, triptolide palmitate, triptolide stearate, triptolide arachidonate, triptolide behenate, and triptolide linolenate, were developed. The liposome encapsulation rate of these six triptolide lipid-soluble prodrugs was greater than 90%, and the in vivo antitumor efficacy study revealed that the tumor inhibition rate of the lipid-soluble prodrugs was significantly greater than that of the control group of triptolide, e.g., the tumor inhibition rate of the liposome group of triptolide behenate was 57.1%, and that of the control group of the original drug of triptolide was 17.67%.

In summary, to improve the drug-forming properties of triptolide, the use of triptolide lipid-soluble prodrugs and their nanoformulations are important research directions because of the good stability and biosafety of saturated fatty acids. Therefore, the saturated fatty acid esters of triptolide are the focus of research. However, to date, research on saturated fatty acid esters in triptolide has not yet been perfected, and no systematic and meticulous studies have been carried out, especially regarding their antitumor effectiveness and safety, which need to be further improved, especially for triptolide, a highly active and toxic drug whose antitumor efficacy and safety are particularly important.

CONTENT OF THE PRESENT INVENTION

To address the limitations of the existing technology, to improve the technology of utilizing saturated fatty acid esters of triptolide and to provide more effective and safe fatty acid esters of triptolide and their preparations for use in the clinic, the present invention provides a kind of triptolide lignocerate and a liposome thereof and a preparation method therefor.

Saturated fatty acids can be classified into short-chain fatty acids (C2-C4), medium-chain fatty acids (C6-C12), long-chain fatty acids (C14-C20), and very long-chain fatty acids (C22-C26) on the basis of the length of the fatty acid carbon chain. Fu Zhiqin et al. (Chinese Patent CN106946975) reported saturated fatty acid esters of the C4-C18 chain length of triptolide, and Huang Zhiyong (Fatty acid chain length affects the liposomal properties of triptolide prodrugs [D]. 2020) reported saturated fatty acid esters of the C14-C22 chain length of triptolide, and thus far, no studies have been conducted on triptolide lignocerate (C24) and triptolide waxy acid esters (C26). Owing to the problems of metabolism and safety in vivo due to the long carbon chain of waxy acid (hexacosanoic acid), its content in vivo must be strictly controlled, and the normal range of blood concentration is 0.3-0.7 μmol/L (Wei Hong. Establishment and application of GC-MS method for the determination of plasma very long-chain fatty acids[J]. Journal of Clinical Pediatrics, 2005(08):25-28.), which undoubtedly greatly limits its clinical application. Therefore, the present inventors carried out a comparative study with other related saturated fatty acid esters of triptolide with respect to the use of triptolide lignocerate.

The present inventor selected the preferred triptolide stearate disclosed in the Chinese patent document CN106946975A and the literature (Huang Zhiyong. A study on the effects of fatty acid chain length on the liposome properties of triptolide predrug [D]. 2020) revealed that when triptolide arachidonate and triptolide behenate were used as controls, a series of saturated fatty acid esters of triptolide, including triptolide lignocerate (Example 1), were synthesized, and these compounds were prepared into liposome nano-preparations (Example 3); unexpectedly, an in vivo antitumor efficacy study revealed that the antitumor effect of triptolide lignocerate was the strongest, and its tumor inhibition rate was significantly greater than that of triptolide stearate, arachidonate, and behenate and was unexpectedly found to be the best in terms of safety (Example 5). A subsequent pharmacokinetic study demonstrated that the in vivo half-life of triptolide lignocerate was longer than that of the other fat-soluble derivatives of triptolide (Example 6). Therefore, in the present study, the antitumor efficacy and safety of liposomes of triptolide lignocerate were significantly greater than those of the disclosed saturated fatty acid esters of the triptolide derivative, which further enhances the technological advantages of the lipid-soluble derivatives and their nano-preparations and further enhances the space of the druggability of triptolide, which is a high-activity and high-toxicity drug that has a clear advantage.

In the process of synthesizing the triptolide lignocerate by the present inventors, when Example 1 in the patent document CN106946975A was adopted, the synthesis yield was low (52.1%). Surprisingly, the solubility of lignoceric acid in the reaction system could be effectively improved by controlling the temperature and reaction time, and the triptolide lignocerate could be obtained in high yield (Example 7).

A first object of the present invention is to provide a triptolide derivative, specifically a triptolide lignocerate, with a chemical structure, as shown in formula (I):

formula (I)

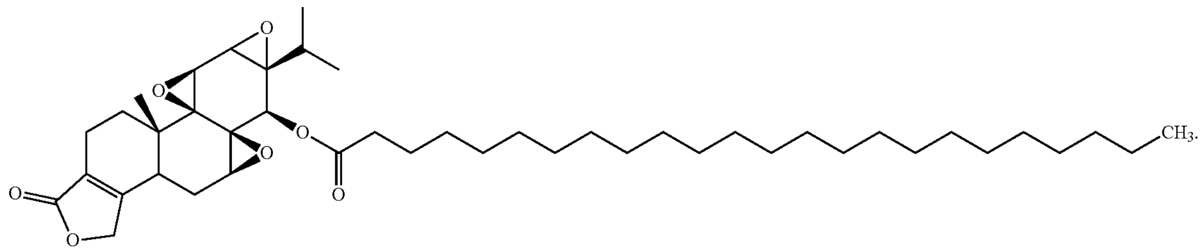

A second object of the present invention is to provide a preparation method for the triptolide lignocerate, said triptolide lignocerate can be obtained by esterification reaction of TP with lignoceric acid by the synthetic route:

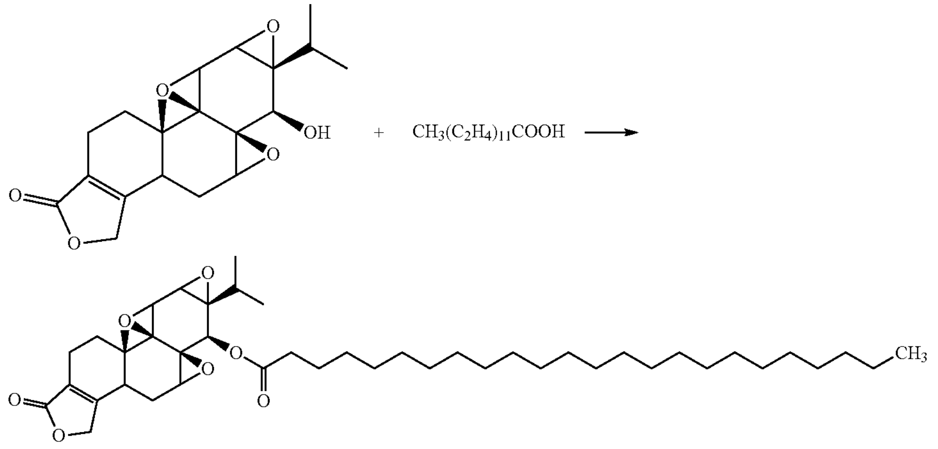

The specific preparation method is as follows: Weighing lignoceric acid and an acid-binding agent, dissolving them in an appropriate amount of anhydrous DCM, and stirring at room temperature to obtain a mixed solution; Weighing a catalyst and dissolving it in the above mixed solution, and stirring and mixing evenly; Dissolving triptolide in an appropriate amount of anhydrous DCM and slowly adding to the above mixed solution, heating in an oil bath and continuing the reaction under nitrogen protection; Rinsing the reaction mixture twice with saturated $NaHCO_3$ solution and saturated NaCl solution respectively, removing the residual moisture with anhydrous $Na_2SO_4$ after separation, removing DCM by rotary evaporation and finally purifying by silica gel column chromatography to obtain the triptolide lignocerate.

Said acid-binding agent is one or more of 1-(3-dimethylaminopropyl)-3-ethylcarbodiimide hydrochloride, N,N'-dicyclohexyl carbodiimide, 4-nitrobenzoyl chloride and N,N'-diisopropyl carbodiimide, preferably 1-(3-dimethylaminopropyl)-3-ethylcarbodiimide hydrochloride.

Said catalyst is one or more of 4-pyrrolidinopyridine, 4-dimethylaminopyridine, N,N-diisopropylethylamine and 1-hydroxybenzotriazole, preferably 4-dimethylaminopyridine.

Said molar ratio of lignoceric acid to triptolide is 2:1 to 6:1, preferably 3:1 to 4:1.

Said molar ratio of acid-binding agent to triptolide is 2:1 to 6:1, preferably 3:1 to 5:1.

Said temperature of the oil bath is 25 to 80° C., preferably 60 to 80° C.

Said reaction time is 8 to 24 h, preferably 12 to 18 h.

A third object of the present invention is to provide a nano-preparation of triptolide lignocerate, said nano-preparation being triptolide lignocerate liposomes, polymer micelles, albumin nanoparticles, fat emulsions and the like.

Said nano-preparation is an injection or a lyophilized powder for injection, preferably a lyophilized powder for injection.

Said liposomes of triptolide lignocerate, with triptolide lignocerate as a main drug, and further including lecithin and the like.

The described triptolide lignocerate liposomes have a drug-to-lipid ratio of 1:5-1:30 (w/w), and are specifically prepared from the following formulation:

| | |
|---|---|
| Triptolide lignocerate | 0.05-1% (w/v) |
| Lecithin | 0.5-10% (w/v) |
| DSPE-PEG2000 | 0-1% (w/v) |
| Electrolyte | 0-0.05% (w/v) |
| Organic solvent | 0.1-15% (w/v) |
| Lyoprotectant | 0-40% (w/v) |
| Water for Injection | tolerance. |

Preferably, said liposomes of triptolide lignocerate have a drug-to-lipid ratio of 1:10-1:20 (w/w), and are specifically prepared from the following formulation:

| | |
|---|---|
| Triptolide lignocerate | 0.1-0.5% (w/v) |
| Lecithin | 1-5% (w/v) |
| DSPE-PEG2000 | 0-0.5% (w/v) |
| Electrolyte | 0-0.01% (w/v) |
| Organic solvent | 0.5-5% (w/v) |
| Lyoprotectant | 10-30% (w/v) |
| Water for Injection | tolerance. |

Wherein the lecithin described in the above formulation is selected from one or more of high-purity egg yolk lecithin, hydrogenated soybean lecithin, dipalmitoyl phosphatidylcholine, phosphatidylcholine, soy lecithin, phosphatidylserine, dimyristoyl phosphatidylcholine, distearoyl phosphatidylcholine, phosphatidylethanolamine and sphingomyelin; preferably, high-purity egg yolk lecithin.

The organic solvent described in the above formulation is selected from one or more of anhydrous ethanol, propylene glycol, tert-butanol, chloroform, dichloromethane, preferably anhydrous ethanol, preferably in an amount of 0.5-5% (w/v).

The electrolyte described in the above formulation is selected from one or more of sodium citrate, $Na_2SO_4$, NaCl, $Na_2CO_3$, $FeCl_3$, $Na_3PO_4$, preferably NaCl, preferably in an amount of 0-0.01% (w/v).

The lyoprotectant described in the above formulation is one or more of tremalose, sucrose, maltose, lactose, mannitol, glucose, sorbitol, xylitol, erythritol, threonine; preferably one or more of tremalose, sucrose, maltose, preferably in an amount of 10-30% (w/v).

A fourth object of the present invention is to provide a preparation method for a triptolide lignocerate liposome.

The described preparation method for the triptolide lignocerate liposome is an injection method and is prepared by the following steps:

Weighing the prescribed amount of triptolide lignocerate, lecithin, and DSPE-PEG2000, placing them in an organic solvent for injection, and heating at 25-60° C. to dissolve, obtaining an organic phase; Weighing the prescribed amount of electrolyte into an appropriate amount of water for injection, heating and stirring at 25-60° C. to dissolve, obtaining an aqueous phase; Under stirring conditions, slowly injecting the aqueous phase into the organic phase or slowly injecting the organic phase into the aqueous phase, mixing uniformly to obtain a crude liposome; Emulsifying the crude liposome, by homogenizing emulsification using a high-pressure homogenizer, or by placing in an extruder and extruding successively through extrusion membranes with different pore sizes, or by homogenizing under high pressure first and then extruding, to obtain a liposome solution; Making up the volume with water for injection, filtering through a 0.22 μm membrane for sterilization, dispensing, sealing, and caping to obtain triptolide lignocerate liposome injection; Alternatively, weighing the prescribed amount of lyoprotectant, placing it in the liposome solution, stirring to dissolve, making up the volume with water for injection, filtering through a 0.22 μm membrane for sterilization, dispensing, freeze-drying, sealing, and caping to obtain triptolide lignocerate liposome lyophilized powder for injection.

The crude liposome is emulsified as described, preferably by extrusion emulsification method, and the liposome particle size distribution obtained will be more uniform; the pore size of the extruded membrane is selected from 0.8 μm, 0.6 μm, 0.4 μm, 0.2 μm, 0.1 μm, 0.05 μm, and one or more of extruded membrane are selected to be extruded sequentially from larger to smaller pore sizes, preferably 0.4 μm, 0.2 μm, 0.1 μm, 0.05 μm.

The organic solvent for injection, as described, may be retained in the liposome, or may be removed by ultrafiltration after emulsification of the crude liposome, or may be removed by freeze-drying.

Said electrolyte can be dissolved in an aqueous phase or in a liposome solution, preferably in an aqueous phase.

Said lyoprotectant can be dissolved in an aqueous phase or in a liposome solution.

Said liposomes of triptolide lignocerate have a particle size of 50-150 nm.

Said triptolide lignocerate can also be prepared into nano-delivery preparations such as polymer micelles, albumin nanoparticles, fat emulsions and the like.

A fifth object of the present invention is to provide a use of said triptolide lignocerate, said nano-preparations of triptolide lignocerate in the preparation of anti-tumor drugs.

The advantages of this invention are:

1. Stronger efficacy: triptolide is an antitumor drug, antitumor efficacy has always been the first element of antitumor drug screening research, triptolide lignocerate liposome and its tumor inhibition rate is not only higher than the other saturated fatty acid esters of triptolide (Example 5), but also higher than the current foreign clinical studies of the third phase of the Minnelide (Example 55), with a clear advantage of efficacy.
2. Lower toxicity: The high toxicity of triptolide severely limits its clinical application, while liposomal in vitro and in vivo studies of triptolide lignocerate show that its toxicity is significantly lower than that of other lipid-soluble predrugs of triptolide, with obvious safety advantages.
3. Stronger slow-release effect, longer half-life: triptolide has a short half-life (15 min) and is rapidly eliminated in vivo, while the slow-release effect of triptolide lignocerate liposomes in the in vitro release study was significantly stronger than that of other lipid-soluble prodrugs of triptolide (Example 4); in the in vivo pharmacokinetic study, triptolide lignocerate liposomes have a longer in vivo half-life than that of other lipid-soluble prodrugs of triptolide (Example 6).
4. The preparation process is smoother: the invention preparation research process, through the organic solvent dosage control (Example 16), optimization of the drug-to-lipid ratio (Example 17), and addition of appropriate amounts of electrolytes (Example 18) resulted in smaller and more homogeneous liposome particle size and smoother preparation process.

DETAILED DESCRIPTION OF THE PREFERRED EMBODIMENT

Figure 1:
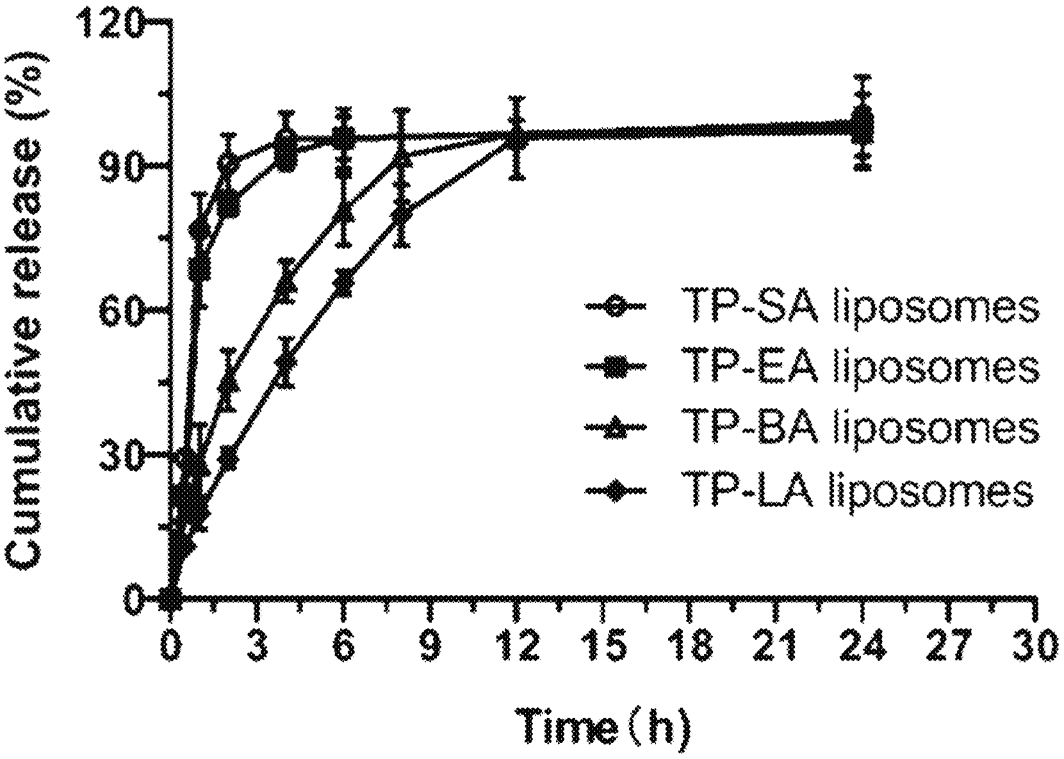
FIG. 1 shows the in vitro release graph of liposomes of different triptolide derivatives of Example 4.
Figure 2:
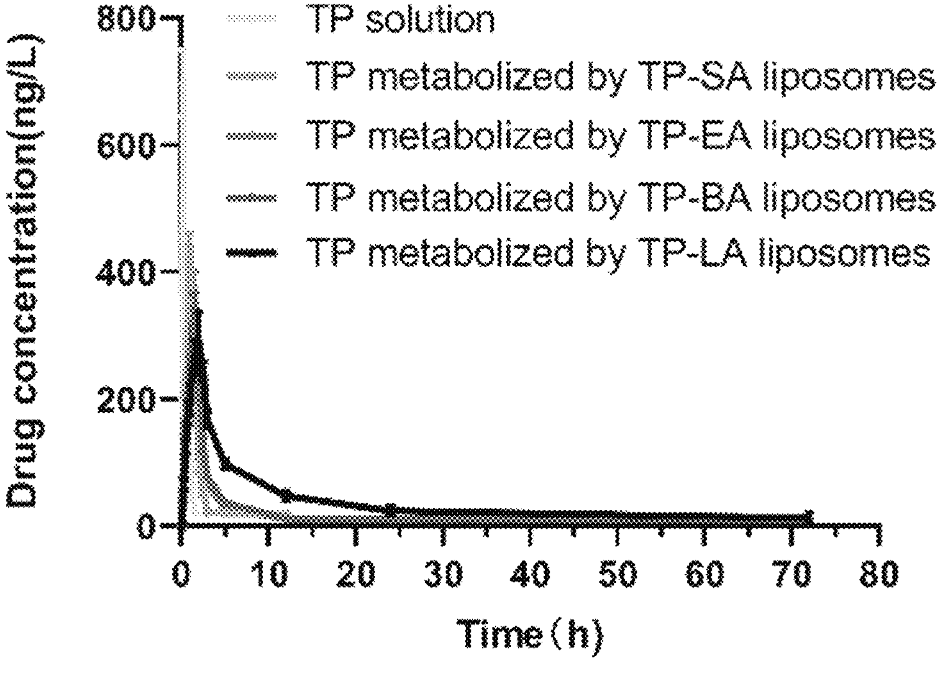
FIG. 2 shows a graph of blood concentration over time in rats in Example 6.

The detailed description of the preferred embodiment of the present disclosure will be described in detail in conjunction with the following examples. It should be understood that the following examples are only intended to illustrate the present disclosure, but not to limit the scope of the present disclosure. The following examples do not specify the particular conditions of the experimental methods, generally according to conventional conditions, or according to the manufacturer's suggested conditions.

Example 1: Preparation of a Triptolide Derivative

1. Experimental Prescription

TABLE 1

Prescription design of the experimental validation protocol

| component | Input amount | Prescription 1 | Prescription 2 | Prescription 3 | Prescription 4 |
|---|---|---|---|---|---|
| TP | 1.0 mmol | TP | TP | TP | TP |
| Saturated fatty acid | 3.0 mmol | Stearic acid | Arachidic acid | Behenic acid | Lignoceric acid |
| N,N'-dicyclohexyl carbodiimine | 3.0 mmol | DCC | DCC | DCC | DCC |
| 4-dimethyl-aminopyridine | 3.0 mmol | DMAP | DMAP | DMAP | DMAP |
| Anhydrous DCM | 20 mL | DCM | DCM | DCM | DCM |

2. Preparation Process

According to the preparation method of Patent CN 106946975 embodiment 1, the prescribed amount of saturated fatty acids, N,N'-dicyclohexyl carbodiimide, 4-dimethylampyridine were added into the reaction vessel, 20 mL anhydrous DCM was added, stirred for 30 min, the prescribed amount of TP was dissolved in appropriate anhydrous DCM and slowly dropped to the reaction system, and the reaction was carried out under ice bath for 30 min, the reaction was continued overnight at room temperature, the reaction material was separated and purified by silica gel column.

3. Experimental Results (1) The triptolide stearate TP-SA, a light yellow solid powder, 519.3 mg. The yield rate was 82.90%

ESI-MS (m/z): 627.43 $[M+H]^+$; .

$^1$HNMR (400 MHz, $CDCl_3$) δ 5.09 (s, 1H), 4.68 (s, 2H), 3.83 (d, J=2.9 Hz, 1H), 3.53 (d, J=2.6 Hz, 1H), 3.46 (d, J=5.5 Hz, 1H), 2.70 (d, J=12.6 Hz, 1H), 2.54-2.25 (m, 3H), 2.24-2.08 (m, 2H), 1.90 (dd, J=16.5, 10.3 Hz, 3H), 1.75-1.62 (m, 2H), 1.57 (dd, J=12.3, 4.8 Hz, 1H), 1.45-1.11 (m, 28H), 1.06 (s, 3H), 0.96 (d, J=6.9 Hz, 3H), 0.92-0.78 (m, 6H).

$^{13}$CNMR (101 MHz, $CDCl_3$) δ 173.41 (2C), 160.28, 125.70, 70.79, 70.17, 63.75, 63.52, 61.23, 59.89, 55.49, 55.15, 40.54, 35.85, 34.52, 32.09, 29.98, 29.92-29.75 (8C), 29.65, 29.50 (2C), 29.17, 28.27, 25.18, 23.62, 22.86, 17.52, 17.05, 16.71, 14.12, 13.68.

The chemical structure is shown in the following formula (II):

formula (II)

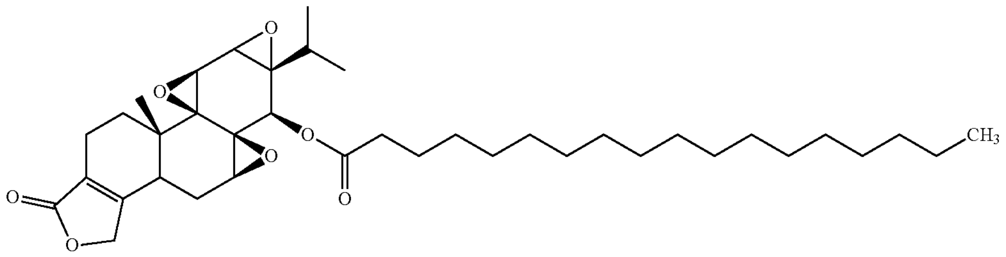

TP-SA (2) The triptolide arachidonate TP-EA, a light yellow solid powder, 532.8 mg. The yield rate was 81.79%.

ESI-MS (m/z): 652.44 $[M+H]^+$;

$^1$HNMR (400 MHz, $CDCl_3$) δ 5.02 (s, 1H), 4.71-4.49 (m, 2H), 3.76 (d, J=3.0 Hz, 1H), 3.46 (d, J=2.8 Hz, 1H), 3.39 (d, J=5.6 Hz, 1H), 2.70-2.55 (m, 1H), 2.50-2.20 (m, 3H), 2.20-1.98 (m, 2H), 1.94-1.72 (m, 2H), 1.70-1.56 (m, 3H), 1.52 (d, J=4.9 Hz, 1H), 1.49 (d, J=4.9 Hz, 1H), 1.36-1.10 (m, 31H), 0.99 (s, 3H), 0.89 (d, J=7.0 Hz, 3H), 0.81 (t, J=6.8 Hz, 3H), 0.77 (d, J=6.9 Hz, 3H).

$^{13}$CNMR (101 MHz, $CDCl_3$) δ 173.47 (2C), 160.26, 125.80, 70.82, 70.20, 63.80, 63.59, 61.27, 59.94, 55.55, 55.20, 40.60, 35.90, 34.58, 32.14, 30.04, 29.99-29.81 (11C), 29.71 (s), 29.56 (2C), 29.23, 28.31, 25.23, 23.69, 22.91, 17.75, 17.28, 16.94, 14.35, 13.90.

The chemical structure is shown in the following formula (III):

formula (III)

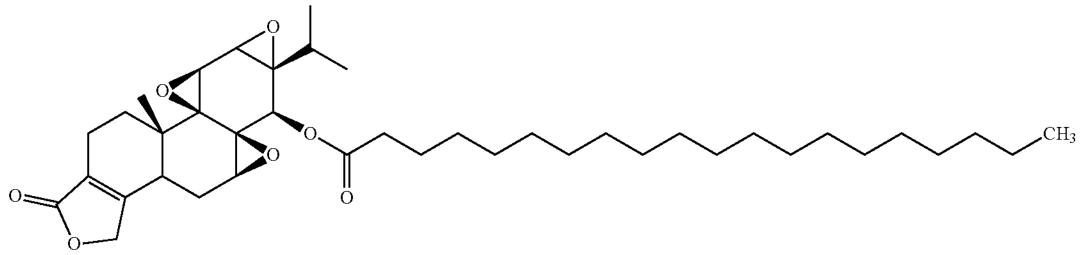

TP-EA (3) The triptolide behenate TP-BA, an off-white solid powder, 594.7 mg. The yield rate was 87.15%.

ESI-MS (m/z): 683.49 $[M+H]^+$;

$^1$HNMR (400 MHz, $CDCl_3$) δ 5.02 (s, 1H), 4.83-4.39 (s, 2H), 3.75 (d, J=3.1 Hz, 1H), 3.46 (d, J=2.7 Hz, 1H), 3.39 (d, J=5.6 Hz, 1H), 2.70-2.55 (m, 1H), 2.33 (tdd, J=23.6, 17.7, 11.8 Hz, 3H), 2.17-1.99 (m, 2H), 1.91-1.75 (m, 2H), 1.68-1.55 (m, 2H), 1.50 (dd, J=12.4, 4.8 Hz, 1H), 1.37-1.08 (m, 36H), 0.99 (s, 3H), 0.89 (d, J=7.0 Hz, 3H), 0.78 (dd, J=12.4, 7.0 Hz, 6H).

$^{13}$CNMR (101 MHz, $CDCl_3$) δ 173.41 (2C), 160.28, 125.69, 70.79, 70.16, 63.75, 63.51, 61.23, 59.89, 55.49, 55.15, 40.54, 35.84, 34.52, 32.09, 29.98, 29.93-29.75 (12C), 29.65, 29.50 (2C), 29.17, 28.27, 25.18, 23.62, 22.86, 17.69, 17.23, 16.88, 14.29, 13.85.

The chemical structure is as described below in the formula (IV):

formula (IV)

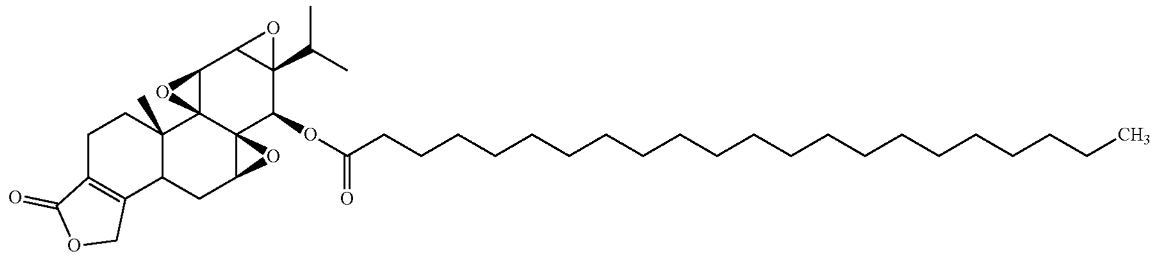

TP-BA (4) The triptolide lignocerate, a light yellow solid powder, 370.7 mg. The yield rate was 52.12%.

ESI-MS (m/z): 711.51 $[M+H]^+$;

$^1$HNMR (400 MHz, $CDCl_3$) δ 7.20 (s, 2H), 5.02 (s, 2H), 4.60 (s, 4H), 3.75 (d, J=3.0 Hz, 2H), 3.46 (d, J=2.4 Hz, 2H), 3.39 (d, J=5.6 Hz, 2H), 2.89 (s, 1H), 1.19 (s, 101H), 0.99 (s, 7H), 0.89 (d, J=7.0 Hz, 7H), 0.84-0.71 (m, 15H).

$^{13}$CNMR (101 MHz, $CDCl_3$) δ 173.21 (d, J=4.4 Hz), 159.97 (s), 125.63 (s), 81.55-81.35 (m), 77.28 (d, J=11.5 Hz), 77.02 (s), 76.70 (s), 70.64 (s), 69.94 (s), 63.60 (s), 63. 39 (s), 61.04 (s), 59.74 (s), 55.33 (s), 55.01 (s), 40.41 (s), 35.71 (s), 34.37 (s), 31.92 (s), 30.00-29.17 (m), 29.06 (d, J=8.7 Hz), 28.15 (s), 25.02 (s), 24.79 (s), 23.50 (s), 22.69 (s), 17.52 (s), 17.08 (s), 16.74 (s), 14.10 (s), 13.69 (s).

The chemical structure is as follows as in the formula (V):

formula (IV)

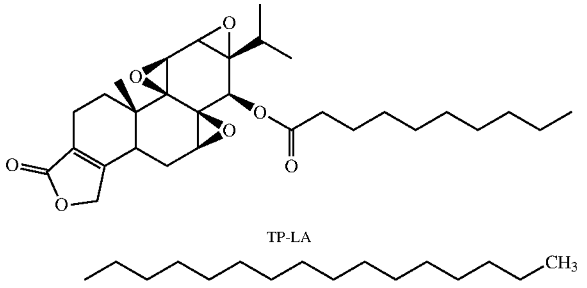

TP-LA

4. Results Analysis

After identification by mass spectrometry, nuclear magnetic resonance hydrogen spectroscopy and carbon spectroscopy, according to the preparation method of Example 1 of Patent CN 106946975, the saturated fatty acid can be bonded to the C14-OH of TP via an acid binding agent and a catalyst to successfully synthesize a series of triptolide derivatives; however, the method in the patent showed that the synthesis yield of the triptolide lignocerate was relatively low (only 52.1%).

Example 2: Determination of Log P Values of Triptolide and Triptolide Derivative 1. Source of Samples TP-SA, TP-EA, TP-BA and TP-LA prepared from prescriptions 1, 2, 3 and 4 in Example 1 were taken as triptolide derivatives and TP as control.

2. Determination of the Log P Values

The log P was determined by shake-flask. First, a certain amount of water and n-octanol are added into the funnel, shaken and separated to obtain water-saturated n-octanol solution and n-octanol saturated aqueous solution; quantify and accurately weigh triptolide and its derivatives in a volumetric bottle containing water-saturated n-octanol solution, and dissolve by ultrasound, drop water-saturated n-octanol solution, dilute and volume. Take 0.5 mL of this solution in a 5 mL volumetric flask, dilute with MeOH and volume. The concentration of triptolide and its derivatives was determined by the assay method; take the above solution to the Xilin bottle, add 10 times the amount of n-octanol saturated aqueous solution, and shake in a bath of 37° C. and 75 rpm for one day, so that triptolide and its derivatives reach equilibrium state in aqueous and organic phase. The n-octanol phase was transferred into a centrifuge tube, centrifuged at 3000 rpm for 10 min, precision measuring n-octanol phase in a volumetric flask, diluted 10 times with MeOH solution, and measured the content of triptolide and its derivatives in n-octanol phase. Drug concentration in the aqueous phase=total drug concentration-drug concentration in the n-octanol phase.

$$\text{Log}P = \text{Log}\left(\frac{\text{drug concentration in the } n\text{-octanol phase}}{\text{Drug concentration in the aqueous phase}}\right)$$

3. The Content Determination Method of Triptolide and Its Derivatives in This Embodiment is Determined by High-Performance Liquid Chromatography (2020 Edition, Chinese Pharmacopoeia's Fourth Part Rule 0512), as Follows:

Chromatographic conditions: using chromatographic column: Agilent ZORBAX Eclipse Plus C18 column (4.6 mm×250 mm, 5 μm), mobile phase: 100% MeOH, column temperature: 30° C., flow rate: 1.0 mL/min, sample input: 20 μL, detection wavelength: 218 nm.

Preparation of control solution: accurately weighing triptolide and its derivatives 10 mg, placed in a 10 mL volumetric flask, dissolved with methanol and diluted to the scale line, shake well, as the control reserve solution.

Preparation of standard curve: Reserve solutions of different volumes of control were diluted to produce series solutions with mass concentrations of 5.00, 10.00, 25.00, 50.00, 100.00, 250.00, and 500.00 μg/mL, respectively. 20 μL of each sample was injected into the HPLC system and analyzed according to the "Chromatographic Conditions". With the concentration C (μg/mL) as the abscissa and the peak area A as the ordinate, the linear regression is obtained.

Assay: accurately absorb 1 mL of each sample solution of triptolide and its derivatives to a 5 mL volumetric flask, dilute with methanol to the scale line, and vortex-mix evenly. 20 μL was injected into the HPLC chromatogram, recorded and calculated by the peak area according to the standard curve method.

4. Experimental Results

TABLE 2

Results of log P determination of TP and different TP derivatives

| TP-FA | log P | RSD (%) |
|---|---|---|
| Triptolide | 0.52 ± 0.01 | 1.92 |
| Triptolide stearate | 2.41 ± 0.04 | 1.66 |
| Triptolide arachidonate | 2.57 ± 0.02 | 0.78 |
| Triptolide behenate | 2.78 ± 0.04 | 1.44 |
| Triptolide lignocerate | 3.12 ± 0.03 | 0.96 |

5. Results Analysis

TP-LA prepared in Example 1 had higher log P values compared to TP-SA, TP-EA, and TP-BA, and TP-LA prepared with TP modified with lignoceric acid was the most lipid-soluble.

Example 3: Liposomes Prepared from Different Triptolide Derivatives

1. Preparation of Liposomes of Different Triptolide Derivatives

TABLE 3

Prescription design of the experimental validation protocol

| Component | Prescription 1 | Prescription 2 | Prescription 3 | Prescription 4 |
|---|---|---|---|---|
| TP Derivative | TP-SA (0.2%) | TP-EA (0.2%) | TP-BA (0.2%) | TP-BA (0.2%) |
| Egg Yolk Phospholipids | 2% | 2% | 2% | 2% |
| PEG of distearoyl ethanolamine | 0.2% | 0.2% | 0.2% | 0.2% |
| Cholesterol | 0.2% | 0.2% | 0.2% | 0.2% |
| Water for injection | To 100 mL | To 100 mL | To 100 mL | To 100 mL |

2. Preparation Process

Referring to the preparation method of Example 2 of Patent CN106946975A. Dissolve 0.2 g of triptolide derivative, 2 g of egg yolk phospholipid, 0.2 g of PEG distearoyl ethanolamine and 0.2 g of cholesterol in an appropriate amount of DCM. The lipid film was removed from the solvent under vacuum evaporation at 45° C.; Hydrate the crude lipids with 80 mL of water for injection; By the crude lipid was emulsified in a high pressure homogenizer to obtain a liposome solution; Weigh up 25 g of trehalose, Dissolve in the above-mentioned liposome solution; Add water for injection to 100 mL, Adjust pH with sodium hydroxide and hydrochloric acid to 6.0; 0.22 μm filter membrane filtration, dispensing, freeze-drying, sealing and capping.

3. Experimental Results

The appearance of liposomes after reconstitution and 0.22 μm filter membrane filtration smoothness were investigated. The results are shown in Table 4 below.

TABLE 4

Results of liposomes from different triptolide derivatives

| Prescription | Appearance | 0.22 μm Filter membrane filtration smoothness | Particle size (nm) | PDI | Encapsulation rate |
|---|---|---|---|---|---|
| Prescription 1 | A translucent homogeneous solution with light blue opalescence | Smooth filtration | 112.1 | 0.168 | 96.3% |
| Prescription 2 | A translucent homogeneous solution with light blue opalescence | Smooth filtration | 116.5 | 0.178 | 96.7% |
| Prescription 3 | A translucent homogeneous solution with light blue opalescence | Smooth filtration | 118.8 | 0.164 | 96.8% |
| Prescription 4 | A translucent homogeneous solution with light blue opalescence | Smooth filtration | 115.2 | 0.171 | 97.2% |

4. Results Analysis

The experimental results showed that liposomes showed good encapsulation of lipid-soluble TP derivatives with a particle size distribution of about 120 nm.

Example 4: In Vitro Release Study of Liposomes of Different Triptolide Derivatives 1. Source of Samples TP-SA liposomes, TP-EA liposomes, TP-BA liposomes and TP-LA liposomes prepared in prescription 1, prescription 2, prescription 3 and prescription 4 in Example 3 were taken as the liposome preparation.

2. In Vitro Release Protocol Design of Liposomes of Different Triptolide Derivatives The release kinetics of triptolide derivatives liposomes were quantitatively examined by drug release assay. This experiment is different from the previous general method of adding aqueous media, Using the oily material n-octanol as the release medium, Add 100 mL of release medium to the 200 mL dissolution cup, 37±0.5° C., The mixing paddle speed is 100 rpm, Heat the oily release medium and be mixed before dispensing, Then the lipid body sample (1 mL) was pipetted in a dissolution cup with appropriate volume release medium, Mixing at constant temperature. 2 mL were sampled at each time point of 0.5, 1, 2, 4, 6, 8, 12 and 24 h, And immediately supplemented with fresh release media. Samples were subsequently filtered with a 0.22 μm nylon filter membrane. 100 μL of sample solution was precisely sucked into a 5 mL volumetric flask, diluted with methanol and fixed in volume, vortexed and mixed for 1 min, the content was measured with 20 μL of sample volume, and an in-vitro cumulative release rate (Er) was calculated.

$$Er(\%) = \frac{C_n V_2 + (C_{n-1} + \cdots + C_2 + C_1)V_1}{L} \times 100\%$$

Where, $C_n$: sample concentration per time point; L: labeled amount of drug product; $V_1$: fixed sampling volume at each time point; $V_2$: volume of release medium.

3. In Vitro Cumulative Drug Release Results

TABLE 5

| Results of in vitro release of liposomes from different triptolide derivatives | | | | |
|---|---|---|---|---|
| Time (h) | TP-SA liposomes | TP-EA liposomes | TP-BA liposomes | TP-LA liposomes |
| 0.5 h | 29.41 ± 1.45 | 21.45 ± 1.99 | 17.89 ± 1.23 | 11.02 ± 0.99 |
| 1 h | 76.80 ± 7.56 | 68.61 ± 8.04 | 27.80 ± 8.48 | 19.85 ± 3.29 |
| 2 h | 90.52 ± 6.02 | 82.09 ± 2.45 | 45.45 ± 6.19 | 32.14 ± 2.06 |
| 4 h | 95.70 ± 5.47 | 92.58 ± 3.12 | 66.09 ± 4.20 | 54.28 ± 5.04 |
| 6 h | 95.69 ± 6.34 | 95.87 ± 4.55 | 80.77 ± 7.21 | 67.80 ± 2.45 |
| 8 h | 97.87 ± 6.55 | 95.88 ± 5.31 | 92.06 ± 9.46 | 90.82 ± 6.45 |
| 12 h | 98.00 ± 7.09 | 96.65 ± 4.80 | 96.80 ± 2.89 | 96.88 ± 8.36 |
| 24 h | 99.04 ± 4.28 | 98.80 ± 6.67 | 97.01 ± 5.08 | 97.41 ± 7.57 |

4. Results Analysis

TP-SA liposomes, TP-EA liposomes, TP-BA liposomes, and TP-LA liposomes prepared by Example 3 were selected to unfold the in vitro release contrast. The experimental results showed that the triptolide derivative liposomes could be fully released in n-octanol, but the cumulative release degree of TP-SA liposomes and TP-EA liposomes reached more than 80% at 2 h, with obvious sudden release phenomenon. Compared with other TP derivative liposomes, TP-LA liposomes slow release effect was more obvious.

Example 5: In Vivo Antitumor Effect of Liposomes of a Triptolide Derivative

Based on the triptolide derivative liposome prepared in Example 3, in a TP (DMSO) solution, and TP-SA liposomes were used as controls for the anti-tumor study of Panc 02 pancreatic cancer model, and the trial design and results are as follows:

1. Source of Samples

TP (DMSO) solution was used as positive control; TP-SA, TP-EA, TP-BA, and TP-LA liposomes prepared from prescriptions 1, 2, 3, and 4 in Example 3 were used as lipid preparations.

2. Establishment of a Mouse Model of Panc02 Pancreatic Cancer and Design of Administration Regimen.

Mouse pancreatic cancer Panc02 cells were cultured in DMEM medium at 37° C., 5% $CO_2$ and passaged on average every two days. During the log growth phase, the cell concentration was adjusted to $1\times10^7$/mL, and Panc 02 cells were subcutaneously seeded in the right axilla of ICR mice under sterile conditions to establish a mouse pancreatic cancer model. When the mouse tumor volume was grown to 100-300 $mm^3$, the mice were randomly divided into 6 groups according to the tumor volume, with 6 mice in each group. The blank, TP (DMSO), TP-SA, TP-EA, TP-BA, and TP-LA were set. The mouse tail vein injection was 0.6 mg/kg (per TP), and the blank group was given 0.2 mL saline every two days for a total of 4 doses. The mice were killed on the third day of drug withdrawal, the mice were weighed, the tumor body was dissected and weighed, and the tumor suppression rate was calculated.

$$\text{Tumor supression rate} = \frac{\text{Tumor weight of the blank group} - \text{Tumor weight in the administration group}}{\text{Tumor weight of the blank group}} \times 100\%$$

3. Anti-Tumor Effect

The results investigated the anti-tumor effect of TP derivative liposomes and TP (DMSO) solution using mouse Panc 02 pancreatic cancer as a model, and the results are shown in Table 6.

TABLE 6

| Comparative anti-tumor results of TP and TP derivative liposomes | | | | |
|---|---|---|---|---|
| Group | Dose (mg/kg) | Body weight change (%) | Mean tumor weight (g) | Tumor Suppression rate (%) |
| Model group | / | 16.70 | 0.878 ± 0.231 | / |
| TP solution group | 0.60 mg/kg | −5.62 | 0.517 ± 0.097 | 41.12% |
| TP-SA liposome | 1.04 mg/kg | 9.39 | 0.452 ± 0.129 | 48.52% |
| TP-EA liposome | 1.08 mg/kg | 10.34 | 0.390 ± 0.093* | 55.58% |
| TP-BA liposome | 1.14 mg/kg | 15.87 | 0.288 ± 0.090*# | 67.20% |
| TP-LA liposome | 1.18 mg/kg | 16.95 | 0.168 ± 0.063**## | 80.86% |

Note:
*P < 0.05,
**P < 0.01 compared to the model group;
#P < 0.05,
P < 0.01 compared to the TP group.

4. Results Analysis

TP-SA liposomes, TP-EA liposomes, TP-BA liposomes, TP-LA liposomes prepared in Example 3 were selected for pharmacodynamic evaluation against the mouse Panc 02 pancreatic cancer model. The experimental results showed that the efficacy of TP-LA liposomes was significantly better than that of TP solution and other TP derivatives; the mice received TP solution, TP-SA liposomes, TP-EA liposomes and TP-BA liposomes, obvious tail swelling and decaying phenomena appear in the mice, resulting in obvious irritation. The mice treated with TP-LA liposome showed no obvious abnormalities and showed a normal weight increase trend, indicating that the overall efficacy and biological safety of the liposomes prepared by the present invention were greatly improved.

Example 6: A Pharmacokinetic Study in Rats

1. Source of Samples

The TP (DMSO) solution was used as a positive control drug, and the TP derivative liposome prepared from Example 3 was taken as a liposome sample.

2. Experimental Design of Pharmacokinetic Experiments in Rats

Rat tail vein dose of equimolar TP 0.6 mg/kg, blood collection time point set at 6 min, 12 min, 18 min, 30 min, 48 min, 1 h, 1.5 h, 2 h, 2.5 h, 3 h, 5 h, 12 h, 24 h, 72 h, 5 SD rats from each group (♂).

Sample processing and analysis method: take plasma with 4 times the amount of methanol to precipitate protein, centrifugation at 12000 r/min for 10 min; remove the supernatant to remove methanol, extract the remaining residue with 400 μL methyl-t-butyl ether twice, centrifugation at 12000 r/min for 10 min. The organic extraction phase was collected, concentrated and dried, 100 μL of methanol was added for redissolution, and the supernatant was centrifuged into the LC-MS/MS system to calculate the plasma concentration by using DAS 2.0 software. The pharmacokinetic parameters are shown in Table 7.

3. Pharmacokinetic Parameters

TABLE 7

Pharmacokinetic results of liposome metabolism of TP solution and TP derivatives

| Parameter | unit | TP solution | TP-SA Liposomes | TP-EA Liposomes | TP-BA Liposomes | TP-LA Liposomes |
|---|---|---|---|---|---|---|
| $C_{max}$ | ng/L | 697.686 ± 67.12 | 441.125 ± 35.18 | 376.125 ± 46.19 | 342.378 ± 76.28 | 293.1223 ± 40.87 |
| $AUC_{0-\infty}$ | ng/L*h | 336.569 ± 37.60 | 704.315 ± 68.94 | 976.253 ± 67.03 | 1488.436 ± 120.08 | 2719.967 ± 168.42 |
| $t_{\frac{1}{2}}$ | h | 0.220 ± 0.04 | 1.349 ± 0.13 | 3.315 ± 0.23 | 8.166 ± 0.45 | 9.651 ± 1.74 |
| V | L/kg | 566.793 ± 70.24 | 1658.397 ± 101.32 | 2940.011 ± 110.08 | 4750.123 ± 146.23 | 3071.977 ± 230.610 |
| CL | L/kg/h | 1782.698 | 851.892 | 614.595 | 403.108 | 220.591 |
| MRT | h | 0.547 ± 0.06 | 3.583 ± 0.48 | 6.246 ± 0.89 | 25.421 ± 1.21 | 23.790 ± 2.130 |

4. Results Analysis

The experimental results showed that TP-LA liposomes have a larger AUC and a longer half-life than other TP derivatives liposomes, as well as the TP solution.

Finally, triptolide lignocerate prepared with lignoceric acid modified TP extends the in vivo action time compared with other triptolide derivatives, and has more significant anti-tumor efficacy in vivo, as well as the advantages of lower administration irritation and toxicity.

Example 7: The Reaction Temperature is Critical for the Development of the Triptolide Lignocerate Prodrug 1. Experimental Prescription

TABLE 8

Prescription design of the experimental validation protocol

| Component | Prescription 1 | Prescription 2 | Prescription 3 | Prescription 4 | Prescription 5 |
|---|---|---|---|---|---|
| TP | 1 mmol | 1 mmol | 1 mmol | 1 mmol | 1 mmol |
| Lignoceric acid | 3 mmol | 3 mmol | 3 mmol | 3 mmol | 3 mmol |
| 1-(3-dimethylamino propyl)-3-ethylcarbodiimide hydrochloride | 3 mmol | 3 mmol | 3 mmol | 3 mmol | 3 mmol |
| 4-dimethyl-aminopyridine | 3 mmol | 3 mmol | 3 mmol | 3 mmol | 3 mmol |
| Reaction temperature | 0° C. | 25° C. | 40° C. | 60° C. | 80° C. |

2. Preparation Process

The prescribed amount of lignoceric acid, 1-(3-dimethylaminopropyl)-3-ethylcarbodiimide hydrochloride were added to the reaction vessel, Add an appropriate amount of anhydrous DCM to stir and dissolve, the mixtue was stirred at room temperature for 30 min at room temperature. Add a prescribed amount of 4-dimethylaminopyridine to mix evenly in the solution; a prescribed amount of TP was dissolved in moderate amounts of anhydrous DCM and slowly added to the reaction system, The ice or oil bath was heated and reacted with nitrogen protection for 12 h, The reaction solution was washed twice before and after saturated $NaHCO_3$ solution and saturated NaCl solution, After the separation, the residual water was removed with anhydrous $Na_2SO_4$, Rerotating the evaporation to remove the DCM, and the residue was purified by silica gel column chromatography.

3. Experimental Results

The appearance characteristics and yield of the triptolide lignocerate prodrug were investigated, and the results are shown in Table 9 below:

TABLE 9

Results of the effect of reaction temperature on the preparation of triptolide lignocerate

| Prescription | Appearance | Output (g) | Yield rate (%) |
|---|---|---|---|
| Prescription 1 | Light yellow solid powder | 0.350 | 49.3 |
| Prescription 2 | Off-white solid powder | 0.633 | 89.1 |
| Prescription 3 | Off-white solid powder | 0.657 | 92.4 |
| Prescription 4 | Off-white solid powder | 0.677 | 95.3 |
| Prescription 5 | Off-white solid powder | 0.679 | 95.6 |

4. Results Analysis

The results showed that the different reaction temperature affected the yield of the triptolide lignocerate derivatives. When the reaction temperature is low, the lignoceric acid cannot be completely dissolved in the reaction system, which reduces the synthesis yield. When the reaction temperature increases, lignoceric acid is well dissolved and the synthesis yield of triptolide lignocerate is significantly increased. However, considering that the high temperature may introduce reaction impurities and high energy loss, controlling the appropriate reaction temperature is the key of the invention.

Example 8: Preparation of Triptolide Lignocerate (TP-LA)

4.0 mmol lignoceric acid and 5.0 mmol 1-(3-dimethylaminopropyl)-3-ethylcarbodiimide hydrochloride were added to a reaction vessel, and an appropriate amount of anhydrous DCM was added to stir and dissolve, and stirred for 30 min at room temperature, and 4.0 mmol 4-dimethylaminopyridine was added to the solution and mixed evenly; 1.0 mmol TP was dissolved in an appropriate amount of anhydrous DCM and slowly added to the reaction system, and the reaction was continued for 24 h in an oil bath at 70° C. and nitrogen protection, and the reaction solution was washed twice with saturated $NaHCO_3$ solution and saturated NaCl solution, respectively, and the residual water was removed with anhydrous $Na_2SO_4$ after separation, and DCM was removed by rotary evaporation, and finally 0.685 g of triptolide lignocerate was obtained by separation and purification by silica gel column chromatography. The yield was 96.4%.

Example 9: Preparation of Triptolide Lignocerate (TP-LA)

2.0 mmol lignoceric acid and 3.0 mmol N,N'-dicyclohexyl carbodiimide were added to a reaction vessel, and an appropriate amount of anhydrous DCM was added to stir and dissolve. Stir for 30 min at room temperature, and 3.0 mmol 4-dimethylaminopyridine was added to the solution and mixed evenly; 1.0 mmol TP was dissolved in an appropriate amount of anhydrous DCM and slowly added to the reaction system, and the reaction was continued for 12 h in an oil bath at 40° C. and nitrogen protection. The reaction solution was washed twice with saturated $NaHCO_3$ solution and saturated NaCl solution, and the residual water was removed with anhydrous $Na_2SO_4$ after separation, and DCM was removed by rotary evaporation. Finally, 0.662 g of triptolide lignocerate was separated and purified by silica gel column chromatography. Yield 93.2%.

Example 10: Preparation of Triptolide Lignocerate (TP-LA)

6.0 mmol lignoceric acid and 2.0 mmol 1-(3-dimethylaminopropyl)-3-ethylcarbodiimide hydrochloride were added to a reaction vessel, and an appropriate amount of anhydrous DCM was added to stir and dissolve, and stirred for 30 min at room temperature, and 3.0 mmol 4-pyrrolidinopyridine was added to the solution and mixed evenly; 1.0 mmol TP was dissolved in an appropriate amount of anhydrous DCM and slowly added to the reaction system, and the reaction was continued for 8 h in an oil bath at 25° C. and under nitrogen protection, and the reaction solution was washed twice with saturated $NaHCO_3$ solution and saturated NaCl solution, respectively, and the residual water was removed with anhydrous $Na_2SO_4$ after separation, and DCM was removed by rotary evaporation, and finally 0.654 g of triptolide lignocerate was obtained by separation and purification by silica gel column chromatography. Yield 92.1%.

Example 11: Preparation of Triptolide Lignocerate (TP-LA)

Add 4.0 mmol lignoceric acid and 6.0 mmol 1-(3-dimethylaminopropyl)-3-ethylcarbodiimide hydrochloride into the reaction vessel, add an appropriate amount of anhydrous DCM, stir to dissolve, and stir at room temperature for 30 min, add 4.0 mmol 4-dimethylaminopyridine to the solution and mix evenly; dissolve 1.0 mmol TP in an appropriate amount of anhydrous DCM and slowly add it to the reaction system, continue the reaction in a 30° C. oil bath under nitrogen protection for 10 h. The reaction solution was washed twice with $NaHCO_3$ solution and saturated NaCl solution. After separation, the residual water was removed with anhydrous $Na_2SO_4$, and DCM was removed by rotary evaporation. Finally, 0.666 g of triptolide lignocerate was obtained by silica gel column chromatography for separation and purification. The yield is 93.8%.

Example 12: Preparation of Triptolide Lignocerate (TP-LA)

Add 3.0 mmol lignoceric acid and 4.0 mmol 1-(3-dimethylaminopropyl)-3-ethylcarbodiimide hydrochloride into the reaction vessel, add an appropriate amount of anhydrous DCM, stir to dissolve, and stir at room temperature for 30 min, add 4.0 mmol 4-pyrrolidinopyridine to the solution and mix evenly; dissolve 1.0 mmol TP in an appropriate amount of anhydrous DCM and slowly add it to the reaction system, continue the reaction in a 60° C. oil bath under nitrogen protection for 16 hours, and the reaction solution was washed twice with saturated $NaHCO_3$ solution and saturated NaCl solution, respectively. After separation, the residual water was removed with anhydrous $Na_2SO_4$, and then DCM was removed by rotary evaporation. Finally, 0.679 g of triptolide lignocerate was obtained by separation and purification by silica gel column chromatography. The yield is 95.5%.

Example 13: Preparation of Triptolide Lignocerate (TP-LA)

Add 3.0 mmol lignoceric acid and 4.0 mmol 1-(3-dimethylaminopropyl)-3-ethylcarbodiimide hydrochloride into the reaction vessel, add an appropriate amount of anhydrous DCM, stir to dissolve, and stir for 30 min at room temperature. Add 4.0 mmol N,N-diisopropylethylamine and 2.0 mmol 1-hydroxybenzotriazole to the solution and mix evenly; dissolve 1.0 mmol TP in an appropriate amount of anhydrous DCM and slowly add it to the reaction system. The reaction was continued for 8 hours in an 80° C. oil bath under nitrogen protection. The reaction solution was washed twice with saturated $NaHCO_3$ solution and saturated NaCl solution. After separation, the residual moisture was removed with anhydrous $Na_2SO_4$, and then DCM was removed by rotary evaporation. Finally, it was separated and purified by silica gel column chromatography. 0.655 g of triptolide lignocerate was obtained. The yield is 92.2%.

Example 14: Preparation of Triptolide Lignocerate (TP-LA)

Add 3.0 mmol lignoceric acid and 2.0 mmol N,N'-dicyclohexyl carbodiimide into the reaction vessel, add an appropriate amount of anhydrous DCM and stir to dissolve, stir at room temperature for 30 minutes, and add 4.0 mmol 4-dimethylaminopyridine into the solution and mix evenly; dissolve 1.0 mmol TP in an appropriate amount of anhydrous DCM and slowly add it to the reaction system. Continue the reaction in a 40° C. oil bath under nitrogen protection for 16 hours. The reaction solution was washed twice with saturated $NaHCO_3$ solution and saturated NaCl solution, respectively. After separation, the residual water was removed with anhydrous $Na_2SO_4$, and then DCM was removed by rotary evaporation. Finally, 0.661 g of triptolide lignocerate was obtained by separation and purification by silica gel column chromatography. The yield was 93.0%.

Example 15: Preparation of Triptolide Lignocerate (TP-LA)

Add 5.0 mmol lignoceric acid and 5.0 mmol 1-(3-dimethylaminopropyl)-3-ethylcarbodiimide hydrochloride into the reaction vessel, add an appropriate amount of anhydrous DCM, stir to dissolve, and stir at room temperature for 30 min, add 4.0 mmol 4-pyrrolidinopyridine to the solution and mix evenly; dissolve 1.0 mmol TP in an appropriate amount of anhydrous DCM and slowly add it to the reaction system, continue the reaction in a 70° C. oil bath under nitrogen protection for 18 h. The reaction solution was washed twice with saturated $NaHCO_3$ solution and saturated NaCl solution, respectively. After separation, the residual water was removed with anhydrous $Na_2SO_4$, and then DCM was removed by rotary evaporation. Finally, 0.686 g of triptolide lignocerate was obtained by separation and purification by silica gel column chromatography. The yield is 96.6%.

Example 16: The Dosage of Organic Solvent for Injection is Key to the Development of Triptolide Lignocerate Liposomes 1. Experimental Prescription

TABLE 10

Prescription design of the experimental validation protocol

| Components | Prescription 1 | Prescription 2 | Prescription 3 | Prescription 4 | Prescription 5 |
|---|---|---|---|---|---|
| Triptolide lignocerate | 0.30 g | 0.30 g | 0.30 g | 0.30 g | 0.30 g |
| High-purity egg yolk lecithin | 3.00 g | 3.00 g | 3.00 g | 3.00 g | 3.00 g |
| DSPE-PEG2000 | 0.10 g | 0.10 g | 0.10 g | 0.10 g | 0.10 g |
| Anhydrous ethanol | 0.50 g | 3.00 g | 5.00 g | 10.00 g | 15.00 g |
| Water for Injection | to 100 mL | to 100 mL | to 100 mL | to 100 mL | to 100 mL |

2. Preparation Process

Weigh the prescribed amount of triptolide lignocerate, high-purity egg yolk lecithin, and DSPE-PEG2000, place them in the prescribed amount of anhydrous ethanol, and heat to dissolve at 60° C. to obtain the organic phase; weigh an appropriate amount of water for injection, Heat at 60° C. to obtain the aqueous phase; slowly inject the aqueous phase into the organic phase under stirring conditions and mix well to obtain crude liposomes; extrude the crude liposomes through extrusion membranes with pore sizes of 0.4 μm, 0.1 μm, and 0.05 μm respectively to obtain a liposome solution. Weigh 25 g of sucrose, place it in the above liposome solution, stir to dissolve, dilute to 100 mL with water for injection, pass through a 0.22 μm filter membrane to sterilize, dispense, freeze-dry, and cap, to obtain lyophilized powder for injection of triptolide lignocerate liposomes.

3. Experimental Results

The appearance of the above-mentioned liposomes and the filtration smoothness of the 0.22 μm filter membrane were investigated. The results are shown in Table 11:

TABLE 11

Results of the effect of dosage of organic solvent for injection on TP-LA liposomes

| Prescription | Appearance | 0.22 μm Filter membrane filtration smoothness | Particle size (nm) | PDI |
|---|---|---|---|---|
| Prescription 1 | A translucent homogeneous solution with light blue opalescence | Smoother filtration | 145.3 | 0.188 |
| Prescription 2 | A translucent homogeneous solution with light blue opalescence | Smooth filtration | 101.1 | 0.147 |
| Prescription 3 | A translucent homogeneous solution with light blue opalescence | Smooth filtration | 103.4 | 0.130 |
| Prescription 4 | A translucent homogeneous solution with light blue opalescence | Smooth filtration | 115.3 | 0.084 |
| Prescription 5 | A translucent homogeneous solution with light blue opalescence | Smooth filtration | 116.6 | 0.089 |

The appearance and redissolution of the lyophilized powder for injection after direct freeze-drying of the above liposome solution were investigated. The results are shown in Table 12 below:

TABLE 12

Effect of the dosage of organic solvent for injection on freeze-drying of TP-LA liposomes

| Prescription | Appearance | Redissolution time (s) | Particle size after redissolution (nm) | PDI after redissolution |
|---|---|---|---|---|
| Prescription 1 | Shrinkage, collapse | 128 | 147.5 | 0.193 |
| Prescription 2 | Smooth and plump | 34 | 102.2 | 0.141 |
| Prescription 3 | Shrinking, falling off | 52 | 112.6 | 0.152 |
| Prescription 4 | Spray in the bottle | / | / | / |
| Prescription 5 | Spray in the bottle | / | / | / |

4. Result Analysis

The experimental results showed that different doses of organic solvents for injection significantly affected the preparation and particle size distribution of triptolide lignocerate liposomes. When the content of the organic solvent for injection is small, the lipids cannot be completely dissolved even under heated conditions, which affects the druggability of the lipids and increases the extrusion pressure. However, when the content of the organic solvent for injection increases, the particle size of the prepared triptolide lignocerate liposomes increases. The liposome solution is directly freeze-dried and then lyophilized powder for injection spray in the bottle. The amount of organic solvent is the key to the present invention.

Example 17: Comparative Evaluation of Triptolide Lignocerate Liposomes Prepared with Different Drug-to-Lipid Ratios 1. Preparation of Triptolide Lignocerate Liposomes with Different Drug-to-Lipid Ratios

TABLE 13

Prescription design of the validation protocol

| Components | Prescription 1 | Prescription 2 | Prescription 3 | Prescription 4 | Prescription 5 |
|---|---|---|---|---|---|
| Triptolide lignocerate | 0.30 g | 0.30 g | 0.30 g | 0.30 g | 0.30 g |
| High-purity egg yolk lecithin | 1.50 g | 3.00 g | 4.50 g | 6.00 g | 9.00 g |
| DSPE-PEG2000 | 0.10 g | 0.10 g | 0.10 g | 0.10 g | 0.10 g |
| Water for Injection | to 100 mL | to 100 mL | to 100 mL | to 100 mL | to 100 mL |
| Remark | Drug-to-lipid ratio 1:5 | Drug-to-lipid ratio 1:10 | Drug-to-lipid ratio 1:15 | Drug-to-lipid ratio 1:20 | Drug-to-lipid ratio 1:30 |

2. Preparation Process

Take the prescribed amount of triptolide lignocerate, high-purity egg yolk lecithin, DSPE-PEG2000, place 3 g in anhydrous ethanol, heat at 60° C. to dissolve, and obtain the organic phase; take an appropriate amount of water for injection, heat at 60° C. to obtain the aqueous phase; mix the organic phase in the aqueous phase under stirring to obtain the crude liposomes; extrude the crude liposomes through extrusion membranes with pore sizes of 0.4 μm, 0.1 μm, and 0.05 μm respectively to obtain a liposome solution; take 25 g of sucrose in the above liposome solution, and stir to dissolve, and use water for injection to a volume of up to 100 mL, pass through a 0.22 μm filter membrane to sterilize, dispense, freeze-dry, and cap, to obtain lyophilized powder for injection of triptolide lignocerate liposomes.

3. Experimental Results

The extrusion pressure, liposome appearance and particle size distribution for the above liposomes during preparation were investigated, and the results are shown in Table 14 below.

TABLE 14

Comparison of the effects of different drug-to-lipid ratios on triptolide lignocerate liposomes

| Prescription | Appearance | Particle size (nm) | PDI | Extrusion pressure (bar) |
|---|---|---|---|---|
| Prescription 1 | A translucent homogeneous solution with light blue opalescence | 149.10 | 0.280 | 150 |
| Prescription 2 | A translucent homogeneous solution with light blue opalescence | 105.81 | 0.143 | 10 |
| Prescription 3 | A translucent homogeneous solution with light blue opalescence | 110.28 | 0.178 | 30 |
| Prescription 4 | A translucent homogeneous solution with light blue opalescence | 114.82 | 0.228 | 80 |
| Prescription 5 | A translucent homogeneous solution with light blue opalescence | 125.47 | 0.241 | 130 |

4. Result Analysis

Experimental results show that different drug-to-lipid ratios have a greater impact on the particle size distribution and extrusion pressure of triptolide lignocerate liposomes during preparation. When the drug-to-lipid ratio is large, the extrusion pressure, particle size, and PDI of liposomes become significantly larger. When increasing the drug-to-lipid ratio and reducing the drug-to-lipid ratio to 1:10-1:20, there is no significant change in the particle size distribution of the prepared triptolide lignocerate liposomes, so we prefer the drug-to-lipid ratio is 1:10-1:20.

Example 18: Comparative Evaluation of Triptolide Lignocerate Liposomes Prepared with Different Electrolyte Dosages 1. Preparation of Triptolide Lignocerate Liposomes with Different Electrolyte Dosages

TABLE 15

Prescription design of the validation protocol

| Components | Prescription 1 | Prescription 2 | Prescription 3 | Prescription 4 | Prescription 5 |
|---|---|---|---|---|---|
| Triptolide lignocerate | 0.30 g | 0.30 g | 0.30 g | 0.30 g | 0.30 g |

TABLE 15-continued

| Prescription design of the validation protocol | | | | | |
|---|---|---|---|---|---|
| Components | Prescription 1 | Prescription 2 | Prescription 3 | Prescription 4 | Prescription 5 |
| High-purity egg yolk lecithin | 3.00 g | 3.00 g | 3.00 g | 3.00 g | 3.00 g |
| DSPE-PEG2000 | 0.10 g | 0.10 g | 0.10 g | 0.10 g | 0.10 g |
| NaCl | 0 | 10 μg | 50 μg | 100 μg | 500 μg |
| Water for Injection | to 100 mL | to 100 mL | to 100 mL | to 100 mL | to 100 mL |

2. Preparation Process

Weigh the prescribed amount of triptolide lignocerate, high-purity egg yolk lecithin, and DSPE-PEG2000, place them in 3 g of anhydrous ethanol, and heat to dissolve at 60° C. to obtain an organic phase: weigh the prescribed amount of NaCl and add to an appropriate amount of water for injection, heat and stir at 60° C. to dissolve to obtain an aqueous phase; inject the organic phase into the aqueous phase under stirring conditions and mix evenly to obtain crude liposomes; extrude the crude liposomes through extrusion membranes with pore sizes of 0.4 μm, 0.1 μm, and 0.05 μm respectively to obtain a liposome solution. Weigh 25 g of sucrose and place it in the above liposome solution. Stir to dissolve. Dilute to 100 mL with water for injection, pass through a 0.22 μm filter membrane to sterilize, dispense, freeze-dry, and cap, to obtain lyophilized powder for injection of triptolide lignocerate liposomes.

3. Experimental Results

The extrusion pressure, liposome appearance and filtration smoothness of the 0.22 μm filter membrane during the preparation of the above liposomes were investigated. The results are shown in Table 16 below.

TABLE 16

| Effect results of different electrolyte dosages on triptolide lignocerate liposomes | | | | | |
|---|---|---|---|---|---|
| Prescription | Appearance | 0.22 μm filter membrane filter smoothness | Particle size (nm) | PDI | Extrusion pressure (bar) |
| Prescription 1 | A translucent homogeneous solution with light blue opalescence | Smooth filtration | 104.10 | 0.151 | 120.0 |
| Prescription 2 | A translucent homogeneous solution with light blue opalescence | Smooth filtration | 83.81 | 0.089 | 20.0 |
| Prescription 3 | A translucent homogeneous solution with light blue opalescence | Smooth filtration | 82.28 | 0.088 | 10.0 |
| Prescription 4 | A translucent homogeneous solution with light blue opalescence | Smooth filtration | 84.82 | 0.078 | 10.0 |
| Prescription 5 | A translucent homogeneous solution with light blue opalescence | Smooth filtration | 87.47 | 0.101 | 10.0 |

4. Result Analysis

The experimental results showed that different electrolyte dosages significantly affected the particle size distribution of the triptolide lignocerate liposomes. When electrolyte is added to liposome, the particle size and PDI of liposome are significantly smaller. However, as the electrolyte content increased, the particle strength in the prepared triptolide lignocerate liposomes became saturated and the particle size distribution changed unclearly. Therefore, adding the right amount of electrolyte to the liposome is one of the technical features discovered here.

Example 19: Preparation of Triptolide Lignocerate Liposomes

Weigh 0.5 g of triptolide lignocerate, 10 g of high-purity egg yolk lecithin, and 1 g of DSPE-PEG2000 in the prescribed amount and place them in 10 g of anhydrous ethanol, heat at 25° C. to dissolve, and obtain an organic phase; weigh 50 μg of NaCl, place it in an appropriate amount of water for injection, heat and stir at 25° C. to dissolve, and obtain an aqueous phase; slowly inject the aqueous phase into the organic phase under stirring conditions, mix well, and obtain a crude liposome; pass the crude liposome through a high-pressure homogenizer, homogenize it twice at 15000 psi, 20000 psi, and 25000 psi pressures, respectively, to obtain a liposome solution; add an equal amount of water for injection and ultrafilter 5 times to remove the organic solvent, and dilute to 100 ml with water for injection; sterilize through a 0.22 mm filter membrane, dispense, and cap, and obtain a triptolide lignocerate liposome injection.

The average particle size was measured to be 116.1 nm and the PDI was 0.101.

Example 20: Preparation of Triptolide Lignocerate Liposomes

Weigh 0.05 g of triptolide lignocerate and 1 g of hydrogenated soybean lecithin in the prescribed amount, place in 0.1 g of anhydrous ethanol, heat at 60° C. to dissolve, and obtain an organic phase; weigh an appropriate amount of water for injection, heat at 60° C. to obtain an aqueous phase; slowly inject the aqueous phase into the organic phase under stirring conditions, mix well, and obtain a crude liposome: extrude the crude liposome with extrusion membranes with pore sizes of 0.4 μm, 0.1 μm, and 0.05 μm, respectively, to obtain a liposome solution, dilute to 100 mL with water for injection, sterilize through a 0.22 μm filter membrane, dispense, and cap to obtain a triptolide lignocerate liposome injection.

After measurement, the average particle size is 75.8 nm and the PDI is 0.116.

Example 21: Preparation of Triptolide Lignocerate Liposomes

Weigh 0.3 g of triptolide lignocerate, 3 g of high-purity egg yolk lecithin, and 0.4 g of DSPE-PEG2000 in the prescribed amount and place them in 5 g of anhydrous ethanol, heat at 60° C. to dissolve, and obtain an organic phase; weigh an appropriate amount of water for injection, heat at 60° C. to obtain an aqueous phase; slowly inject the aqueous phase into the organic phase under stirring conditions, mix well, and obtain a crude liposome; extrude the crude liposome with extrusion membranes with pore sizes of 0.4 μm, 0.1 μm, and 0.05 μm, respectively, to obtain a liposome solution, add an equal amount of water for injection and ultrafilter 4 times to remove the organic solvent, and dilute to 100 mL with water for injection; sterilize through a 0.22 μm filter membrane, dispense, and cap to obtain a triptolide lignocerate liposome injection.

The average particle size was measured to be 108.9 nm, and the PDI was 0.146.

Example 22: Preparation of Triptolide Lignocerate Liposomes

Weigh 3 g of triptolide lignocerate, 9 g of hydrogenated soybean lecithin, 6 g of dipalmitoyl phosphatidylcholine, and 0.1 g of DSPE-PEG2000 in the prescribed amount, place in 15 g of anhydrous ethanol, heat at 35° C. to dissolve, and obtain an organic phase; weigh an appropriate amount of water for injection and heat at 35° C. to obtain an aqueous phase; slowly inject the organic phase into the aqueous phase under stirring conditions, mix well, and obtain a crude liposome; extrude the crude liposome using extrusion membranes with pore sizes of 0.4 μm, 0.1 μm, and 0.05 μm, respectively, to obtain a liposome solution, add an equal amount of water for injection, ultrafilter 7 times to remove the organic solvent, and dilute to 100 ml with water for injection, sterilize through a 0.22 μm filter membrane, dispense, and cap to obtain a triptolide lignocerate liposome injection.

The average particle size was 148.7 nm and the PDI was 0.188.

Example 23: Preparation of Triptolide Lignocerate Liposomes

Weigh the prescribed amount of triptolide lignocerate 0.1 g, high-purity egg yolk lecithin 1 g, and DSPE-PEG2000 0.1 g and place them in 2 g of anhydrous ethanol, heat at 55° C. to dissolve, and obtain an organic phase; weigh an appropriate amount of water for injection, heat at 55° C. to obtain an aqueous phase; slowly inject the aqueous phase into the organic phase under stirring conditions, mix well, and obtain a crude liposome; pass the crude liposome through a high-pressure homogenizer, homogenize it twice at 15000 psi, 20000 psi and 25000 psi pressures, respectively, to obtain a liposome solution; dilute to 100 ml with water for injection; sterilize through a 0.22 μm filter membrane, dispense, and cap to obtain a triptolide lignocerate liposome injection.

The average particle size was measured to be 70.1 nm and the PDI was 0.141.

Example 24: Preparation of Triptolide Lignocerate Liposomes

Weigh 0.2 g of triptolide lignocerate, 3 g of sphingomyelin, and 0.15 g of DSPE-PEG2000 in the prescribed amount, place in 4 g of anhydrous ethanol, heat at 45° C. to dissolve, and obtain an organic phase; weigh an appropriate amount of water for injection, heat at 45° C. to obtain an aqueous phase; slowly inject the aqueous phase into the organic phase under stirring conditions, mix well, and obtain a crude liposome; extrude the crude liposome with extrusion membranes with pore sizes of 0.4 μm, 0.1 μm, and 0.05 μm, respectively, to obtain a liposome solution. Add an equal amount of water for injection and ultrafilter 4 times to remove the organic solvent, and dilute to 100 mL with water for injection; sterilize through a 0.22 μm filter membrane, dispense, and cap to obtain a triptolide lignocerate liposome injection.

The average particle size was measured to be 96.6 nm and the PDI was 0.138.

Example 25: Preparation of Triptolide Lignocerate Liposomes

Weigh 0.3 g of triptolide lignocerate, high-purity egg yolk lecithin 4 g, and 0.05 g of DSPE-PEG2000 in the prescribed amount and place in 3 g of anhydrous ethanol, heat at 60° C. to dissolve, and obtain an organic phase; weigh an appropriate amount of water for injection, heat at 60° C. to obtain an aqueous phase; slowly inject the aqueous phase into the organic phase under stirring conditions, mix well, and obtain a crude liposome; extrude the crude liposome using extrusion membranes with pore sizes of 0.4 μm, 0.1 μm, and 0.05 μm, respectively, to obtain a liposome solution; dilute to 100 mL with water for injection, sterilize through a 0.22 μm filter membrane, dispense, and cap to obtain a triptolide lignocerate liposome injection.

It was determined that the average particle size was 102.1 nm and the PDI was 0.137.

Example 26: Preparation of Triptolide Lignocerate Liposomes

Weigh 0.7 g of triptolide lignocerate, 5 g of soybean lecithin, 4 g of phosphatidylethanolamine, and 0.15 g of DSPE-PEG2000 in a prescribed amount, place them in 11 g of anhydrous ethanol, and heat them at 50° C. to dissolve them to obtain an organic phase; weigh an appropriate amount of water for injection, heat them at 50° C. to obtain an aqueous phase; slowly inject the aqueous phase into the organic phase under stirring, mix well, and obtain a crude liposome; extrude the crude liposome using extrusion membranes with pore sizes of 0.4 μm, 0.1 μm, and 0.05 μm, respectively, to obtain a liposome solution, and add an equal amount of water for injection and ultrafilter 6 times to remove organic solvent to obtain liposome solution; weigh 500 μg of NaCl to the above liposome solution, stir to dissolve, dilute to 100 ml with water for injection, sterilize through 0.22 mm filter membrane, dispense and cap to obtain triptolide lignocerate liposome injection.

After measurement, the average particle size is 120.3 nm and PDI is 0.115.

Example 27: Preparation of Triptolide Lignocerate Liposomes

Weigh the prescribed amount of triptolide lignocerate 0.5 g, high-purity egg yolk lecithin 6 g, and DSPE-PEG2000 0.3 g and place them in 6 g of anhydrous ethanol, heat at 55° C. to dissolve, and obtain an organic phase; weigh 100 μg of NaCl and place it in an appropriate amount of water for injection, heat and stir at 55° C. to dissolve, and obtain an aqueous phase; slowly inject the aqueous phase into the organic phase under stirring conditions, mix well, and obtain a crude liposome; pass the crude liposome through a high-pressure homogenizer, homogenize it twice at 15000 psi, 20000 psi and 25000 psi pressures, collect the liposome liquid, add an equal amount of water for injection with the same electrolyte concentration as the above water, and ultrafilter 4 times to remove the organic solvent to obtain a liposome solution; dilute to 100 mL with water for injection, sterilize through a 0.22 μm filter membrane, dispense, and cap, and obtain a triptolide lignocerate liposome injection.

The average particle size was measured to be 109.1 nm, and the PDI was 0.102.

Example 28: Preparation of Triptolide Lignocerate Liposomes

Weigh the prescribed amount of triptolide lignocerate 0.4 g, high-purity egg yolk lecithin 4 g, and DSPE-PEG2000 0.1 g and place them in 8 g of anhydrous ethanol, heat at 50° C. to dissolve, and obtain an organic phase; weigh 20 μg of NaCl and place it in an appropriate amount of water for injection, heat and stir at 50° C. to dissolve, and obtain an aqueous phase; slowly inject the aqueous phase into the organic phase under stirring, mix well, and obtain a crude liposome; extrude the crude liposome using extrusion membranes with pore sizes of 0.4 μm, 0.1 μm, and 0.05 μm, respectively, collect liposome liquid, add an equal amount of water for injection with the same electrolyte concentration as the above water, ultrafilter 5 times to remove organic solvent, obtain liposome solution, dilute to 100 mL with injection water; sterilize through 0.22 μm filter membrane, dispense, and cap to obtain a triptolide lignocerate liposome injection.

According to the measurement, the average particle size is 100.1 nm and the PDI is 0.101.

Example 29: Preparation of Triptolide Lignocerate Liposomes

Weigh 0.3 g of triptolide lignocerate, 4 g of high-purity egg yolk lecithin, and 0.1 g of DSPE-PEG2000 in the prescribed amount, then dissolve them in 4 g of anhydrous ethanol. Heat the mixture to 60° C. to facilitate dissolution, thereby obtaining the organic phase. Concurrently, dissolve 50 μg of NaCl in a suitable volume of water for injection and heat-stir at 60° C. to create the aqueous phase. Subsequently, under continuous stirring conditions, gradually add the aqueous phase to the organic phase and mix thoroughly to prepare a crude liposome. The crude liposome is then extruded through filtration membranes with pore sizes of 0.4 μm, 0.1 μm, and 0.05 μm to collect the liposome liquid. An equal volume of injection water with equivalent electrolyte concentration is added and ultrafiltration performed four times to remove any residual organic solvent, resulting in a liposome solution. Finally, dilute this solution to a final volume of 100 mL using water for injection, sterilize through a 0.22 μm filter membrane, dispense, and cap to obtain a triptolide lignocerate liposome injection.

The average particle size was determined as 87.2 nm with a polymer dispersity index (PDI) value recorded at 0.092.

Example 30: Preparation of Triptolide Lignocerate Liposomes

Weigh 0.3 g of triptolide lignocerate, 3 g of high-purity egg yolk lecithin, and 0.05 g of DSPE-PEG2000 in the prescribed amount and place them in 3 g of anhydrous ethanol, heat at 40° C. to dissolve, and obtain an organic phase; weigh 10 μg of NaCl and place it in an appropriate amount of water for injection, heat and stir at 40° C. to dissolve, and obtain an aqueous phase; slowly inject the aqueous phase into the organic phase under stirring conditions, mix well, and obtain a crude liposome; extrude the crude liposome with extrusion membranes with pore sizes of 0.4 μm, 0.1 μm, and 0.05 μm, respectively, collect the liposome liquid, add an equal amount of water for injection with the same electrolyte concentration as the above water, and ultrafilter 4 times to remove the organic solvent to obtain a liposome solution; dilute to 100 mL with water for injection; sterilize through a 0.22 μm filter membrane, dispense, and cap, and obtain a triptolide lignocerate liposome injection.

The average particle size was measured to be 82.7 nm and the PDI was 0.098.

Example 31: Preparation of Triptolide Lignocerate Liposomes

Weigh 0.2 g of triptolide lignocerate, 2 g of hydrogenated soybean lecithin, 1 g of dipalmitoyl phosphatidylcholine, and 0.3 g of DSPE-PEG2000 in the prescribed amount and place them in 2 g of anhydrous ethanol, heat at 55° C. to dissolve, and obtain an organic phase; weigh an appropriate amount of water for injection, heat at 55° C. to obtain an aqueous phase: slowly inject the aqueous phase into the organic phase under stirring conditions, mix well, and obtain a crude liposome: extrude the crude liposome with extrusion membranes with pore sizes of 0.4 μm, 0.1 μm, and 0.05 μm, respectively, to obtain a liposome solution; weigh 20 g of sucrose into the above liposome solution, stir to dissolve, and dilute to 100 ml with water for injection; sterilize through a 0.22 μm filter membrane, dispense, freeze-dry, and cap to obtain a triptolide lignocerate liposome lyophilized powder for injection.

The average particle size was measured to be 85.0 nm and the PDI was 0.139.

Example 32: Preparation of Triptolide Lignocerate Liposomes

Weigh 1 g of triptolide lignocerate, 7 g of high-purity egg yolk lecithin, and 3 g of phosphatidylserine in the prescribed amount, place in 15 g of anhydrous ethanol, heat at 50° C. to dissolve, and obtain an organic phase; weigh an appropriate amount of water for injection, heat at 50° C. to obtain an aqueous phase; slowly inject the aqueous phase into the organic phase under stirring conditions, mix well, and obtain a crude liposome; extrude the crude liposome with extrusion membranes with pore sizes of 0.4 μm, 0.1 μm, and 0.05 μm, respectively, collect the liposome liquid, add an equal amount of water for injection, and ultrafilter 7 times to remove the organic solvent to obtain a liposome solution; weigh 40 g of trehalose, place in the above liposome solution, stir to dissolve, and dilute to 100 mL with water for injection; sterilize through a 0.22 m filter membrane, dispense, freeze-dry, and cap to obtain a triptolide lignocerate liposome lyophilized powder for injection.

The average particle size was measured to be 138.9 nm and the PDI was 0.175.

Example 33: Preparation of Triptolide Lignocerate Liposomes

Weigh 0.5 g of triptolide lignocerate, high-purity egg yolk lecithin 5 g, DSPE-PEG2000 0.05 g in the prescribed amount and place them in 5 g of anhydrous ethanol, heated at 45° C. to dissolve, the organic phase was obtained. Weigh the appropriate amount of water for injection, and heat it at 45° C. to obtain the aqueous phase; slowly inject the organic phase into the aqueous phase under stirring conditions, and mix well, that is, the crude liposome; The crude liposome was extruded by extrusion membrane with pore sizes of 0.4 μm, 0.1 μm and 0.05 μm, respectively, and the liposome liquid was collected. Add an equal amount of water for injection, and ultrafilter 4 times to remove the organic solvent to obtain a liposome solution. Weigh 15 g of sucrose, put it into the above liposome solution, stir to make it dissolve, and then fix it to 100 mL with water for injection. After passing through a 0.22 μm filter membrane for sterilization, cing, freeze-drying, and capping, a triptolide lignocerate liposome lyophilized powder for injection was obtained.

The average particle size was determined to be 125.8 nm, and the PDI was 0.151.

Example 34: Preparation of Triptolide Lignocerate Liposomes

Weigh 0.1 g of triptolide lignocerate, 0.7 g of sphingomyelin, 0.3 g of phosphatidylcholine, and 0.15 g of DSPE-PEG2000 in the prescribed amount and place them in 0.1 g of anhydrous ethanol, and dissolve them by heating at 25° C. to obtain the organic phase; Weigh appropriate amount of water for injection, heat it at 25° C. to obtain the aqueous phase; slowly inject the aqueous phase into the organic phase under stirring conditions, mix well, that is, the crude liposome; The liposome solution was obtained by extruding the crude liposomes through extrusion membranes with pore sizes of 0.4 μm, 0.2 μm, and 0.05 μm, respectively; Weigh 20 g of sucrose, put it into the above liposome solution, stir to make it dissolve, and then set it to 100 mL with water for injection. After passing through a 0.22 μm filter membrane for sterilization, dispensing, freeze-drying, and capping, a triptolide lignocerate liposome lyophilized powder for injection was obtained.

The average particle size was determined to be 70.6 nm, and the PDI was 0.152.

Example 35: Preparation of Liposomes of Triptolide Lignocerate

The organic phase was obtained by weighing a prescribed amount of 0.3 g of triptolide lignocerate, 3 g of high-purity egg yolk lecithin, and 0.25 g of DSPE-PEG2000 in 3 g of anhydrous ethanol, and heating at 45° C. to dissolve; Weigh appropriate amount of water for injection, heat at 45° C., get the aqueous phase; slowly inject the aqueous phase into the organic phase under stirring conditions, mix well, that is, get the crude liposome; The liposome solution was obtained by extruding the crude liposomes through extrusion membranes with pore sizes of 0.4 μm, 0.2 μm, and 0.05 μm, respectively; Weigh 20 g of sucrose, put it into the above liposome solution, stir to make it dissolve, and then fix it to 100 mL with water for injection, then pass it through a 0.22 μm filter membrane for sterilization, dispense, freeze-dry, and cap, a triptolide lignocerate liposome lyophilized powder for injection was obtained.

The average particle size was determined to be 101.4 nm and the PDI was 0.136.

Example 36: Preparation of Liposomes of Triptolide Lignocerate

The organic phase was obtained by weighing the prescribed amount of triptolide lignocerate 3 g, soybean lecithin 15 g, DSPE-PEG2000 1 g, in 15 g of anhydrous ethanol, and heated at 50° C. to dissolve; Weigh an appropriate amount of water for injection and heat at 50° C. to obtain the aqueous phase; The aqueous phase was slowly injected into the organic phase under stirring conditions and mixed well to get the crude liposome; the crude liposome was extruded through the extrusion membrane with pore sizes of 0.4 μm, 0.2 μm and 0.1 μm, respectively, and the liposome liquid was collected, and then added into an equal amount of water for injection and ultrafiltered for 7 times to remove organic solvent, and then the liposome solution was obtained; Weigh 20 g of maltose and 10 g of tremalose, put them in the above liposome solution, stir to dissolve, and then set to 100 mL with water for injection; Pass the 0.22 μm filter membrane for sterilization, dispense, freeze-dry, and cap, a triptolide lignocerate liposome lyophilized powder for injection was obtained.

The average particle size was determined to be 148.8 nm and the PDI was 0.194.

Example 37: Preparation of Liposomes of Triptolide Lignocerate

The organic phase was obtained by weighing a prescribed amount of 0.3 g of triptolide lignocerate, 3 g of high-purity egg yolk lecithin, and 0.5 g of DSPE-PEG2000 in 3 g of anhydrous ethanol, and heating at 55° C. to dissolve; Weigh the appropriate amount of water for injection, heat at 55° C. to obtain the aqueous phase; slowly inject the aqueous phase into the organic phase under stirring conditions, mix well, that is, the crude liposome; The liposome solution was obtained by passing the crude liposome through a high-pressure homogenizer and homogenized twice at 15000 psi, 20000 psi and 25000 psi respectively. 25 g of sucrose was weighed into the above liposome solution, and fixed to 100 mL with water for injection, and then passed through 0.22 μm filter membrane for sterilization, dispense, freeze-dry, and cap, a triptolide lignocerate liposome lyophilized powder for injection was obtained.

The average particle size was determined to be 106.1 nm and the PDI was 0.141.

Example 38: Preparation of Triptolide Lignocerate Liposomes

The organic phase was obtained by weighing a prescribed amount of 0.4 g of triptolide lignocerate, 4 g of high-purity egg yolk lecithin, and 0.05 g of DSPE-PEG2000 in 5 g of anhydrous ethanol, and heating at 60° C. to dissolve; Weigh the appropriate amount of water for injection, heat at 60° C., get the aqueous phase; slowly inject the aqueous phase into the organic phase under stirring conditions, mix well, that is, the crude liposome; The crude liposome was extruded by extrusion membrane with pore sizes of 0.2 μm, 0.1 μm and 0.05 μm, respectively, and the liposome liquid was collected, and an equal amount of water for injection was added and ultrafiltrated for four times to remove organic solvents, and the liposome solution was obtained. Weigh 10 g of sucrose and 10 g of trehalose into the above liposome solution, and then volume it to 100 mL with water for injection; pass it through a 0.22 μm filter membrane for sterilization, dispense, freeze-dry, and cap, a triptolide lignocerate liposome lyophilized powder for injection was obtained.

The average particle size was determined to be 115.8 nm with a PDI of 0.149.

Example 39: Preparation of Triptolide Lignocerate Liposomes

Weigh the prescribed amount of triptolide lignocerate 0.1 g, hydrogenated soybean phospholipids 2 g, DSPE-PEG2000 0.5 g, in 5 g of tert-butanol, heated at 60° C. to dissolve, to obtain the organic phase; Weigh the appropriate amount of water for injection, heat at 60° C. to obtain the aqueous phase; slowly inject the aqueous phase into the organic phase under stirring conditions, mix well, that is, the crude liposome; The liposome solution was obtained by extruding the crude liposomes through extrusion membranes with pore sizes of 0.4 μm, 0.2 μm, and 0.1 μm, respectively; Weigh 20 g of maltose and 10 g of sucrose into the above liposome solution, stir until dissolved, and then volume to 100 mL with water for injection, sterilize by passing through a 0.22 μm filter membrane, dispensing, freeze-drying and capping, i.e. obtaining a triptolide lignocerate liposome lyophilized powder for injection.

The average particle size was determined to be 76.6 nm, and the PDI was 0.142.

Example 40: Preparation of Triptolide Lignocerate Liposomes

Weighed 0.3 g of the prescribed amount of triptolide lignocerate, 4 g of high-purity egg yolk lecithin, and 0.1 g of DSPE-PEG2000 in 5 g of propylene glycol, and heated at 45° C. to dissolve, the organic phase was obtained; Weigh the appropriate amount of water for injection, heat at 45° C. to obtain the aqueous phase; slowly inject the aqueous phase into the organic phase under stirring conditions, mix well, that is, the crude liposome; The crude liposome was extruded by extrusion membrane with pore sizes of 0.4 μm, 0.2 μm and 0.05 μm, respectively, and the liposome liquid was collected, and an equal amount of water for injection was added and ultrafiltrated for four times to remove organic solvents, and the liposome solution was obtained. Weigh 20 g of tremalose, put it into the above liposome solution, stir until dissolved, and then set it to 100 mL with water for injection; pass it through 0.22 μm filter membrane for sterilisation, dispensing, freeze-drying, and capping, then it was obtained as a triptolide lignocerate liposome lyophilized powder for injection.

The average particle size was determined to be 110.5 nm and the PDI was 0.155.

Example 41: Preparation of Triptolide Lignocerate Liposomes

The prescription amount of triptolide lignocerate 0.9 g, high purity egg yolk lecithin 6 g, phosphatidylcholine 4 g, DSPE-PEG2000 0.15 g, placed in 10 g anhydrous ethanol, heated at 50° C. to dissolve to obtain the organic phase. 50 μg NaCl was placed in an appropriate amount of water for injection, heated and stirred at 50° C. to dissolve to obtain the aqueous phase. The aqueous phase was slowly injected into the organic phase under stirring conditions and mixed well to obtain the crude liposome. The crude liposome was homogenized three times under the pressure of 15000 psi, 20000 psi and 25000 psi respectively by high pressure homogenizer, and the liposome liquid was collected. The same amount of water for injection with the same electrolyte concentration as the above water was added to remove the organic solvent by ultrafiltration for 5 times to obtain the liposome solution. 30 g of maltose was weighed into the above liposome solution, and the volume was determined to 100 mL with water for injection. The liposome solution was sterilized by 0.22 μm filter membrane, dispensed, lyophilized and capped, that is, a triptolide lignocerate liposome lyophilized powder for injection.

The average particle size was 140.4 nm and the PDI was 0.167.

Example 42: Preparation of Triptolide Lignocerate Liposomes

The prescription amount of triptolide lignocerate 0.4 g, high purity egg yolk lecithin 4 g, DSPE-PEG2000 0.2 g, placed in 6 g anhydrous ethanol, heated at 50° C. to dissolve to obtain the organic phase. 50 μg of NaCl was weighed and placed in the appropriate amount of water for injection. The aqueous phase was obtained by heating and stirring at 50° C. to dissolve it. The aqueous phase was slowly injected into the organic phase under stirring conditions, and the crude liposome was obtained by mixing. The crude liposome was extruded with extrusion membranes with pore sizes of 0.4 μm, 0.1 μm, and 0.05 μm, respectively, and the liposome liquid was collected. The same amount of water for injection with the same electrolyte concentration as the above water was added to remove the organic solvent by ultrafiltration for 4 times to obtain the liposome solution. 30 g of sucrose was weighed and placed in the above liposome solution, stirred to dissolve, and diluted to 100 mL with water for injection. After 0.22 μm filter membrane sterilization, dispensing, freeze-drying and capping, a triptolide lignocerate liposome lyophilized powder for injection was obtained.

The average particle size was 96.8 nm and PDI was 0.089.

Example 43: Preparation of Triptolide Lignocerate Liposomes

Weighed the prescription amount of triptolide lignocerate 0.5 g, sphingomyelin 2 g, phosphatidylcholine 3 g, DSPE-PEG2000 0.2 g, placed in 10 g anhydrous ethanol, heated at 45° C. to dissolve, get the organic phase; Weighed NaCl 500 μg in the right amount of water for injection, heated and stirred at 35° C. to dissolve, get the aqueous phase; the aqueous phase was slowly injected into the organic phase under stirring conditions, and the crude liposome was obtained by mixing. The crude liposomes were extruded with extrusion membranes with pore sizes of 0.4 μm, 0.1 μm, and 0.05 μm, respectively. The liposome liquid was collected, and the same amount of water for injection with the same electrolyte concentration as the above water was added. Ultrafiltration 5 times to remove organic solvents to obtain a liposome solution. Sucrose 25 g was weighed and placed in the above liposome solution, stirred to dissolve, and diluted to 100 mL with water for injection. After passing through a 0.22 μm filter membrane for sterilization, dispensing, freeze-drying, and capping, a triptolide lignocerate liposome lyophilized powder for injection was obtained.

The average particle size was 115.2 nm and the PDI was 0.098.

Example 44: Preparation of Triptolide Lignocerate Liposomes

Weigh the prescription amount of triptolide lignocerate 0.3 g, high-purity egg yolk lecithin 5 g, placed in 5 g propylene glycol, heated at 40° C. to dissolve, get the organic phase; 100 μg of NaCl was weighed and placed in an appropriate amount of water for injection, and dissolved by heating and stirring at 40° C. to obtain the aqueous phase.

Under stirring conditions, the aqueous phase was slowly injected into the organic phase and mixed to obtain the crude liposome. The crude liposome was extruded with extrusion membranes with pore sizes of 0.4 μm, 0.1 μm, and 0.05 μm, respectively. The liposome liquid was collected, and the same amount of water for injection with the same electrolyte concentration as the above water was added. Ultrafiltration was used to remove organic solvents for 4 times to obtain the liposome solution. Trehalose 20 g was weighed and placed in the above-mentioned liposome solution, stirred to dissolve, and diluted to 100 mL with water for injection, then sterilized by 0.22 μm filter membrane, dispensed, freeze-dried and capped, that is, a triptolide lignocerate liposome lyophilized powder for injection.

The average particle size was 86.1 nm and PDI was 0.087.

Example 45: Preparation of Triptolide Lignocerate Liposomes

The prescription amount of triptolide lignocerate 0.1 g, dipalmitoyl phosphatidylcholine 1 g, DSPE-PEG2000 0.5 g, placed in 1 g anhydrous ethanol, heated at 30° C. to dissolve to obtain the organic phase. An appropriate amount of water for injection was weighed and heated at 30° C. to obtain an aqueous phase. The aqueous phase was slowly injected into the organic phase under stirring conditions, and the crude liposome was obtained by mixing. The crude liposome was homogenized twice at 15000 psi, 20000 psi and 25000 psi by high pressure homogenizer to obtain liposome solution. $Na_2SO_4$ 500 μg and maltose 30 g were weighed and placed in the above liposome solution, stirred to dissolve, and diluted to 100 mL with water for injection. After 0.22 μm filter membrane sterilization, dispensing, freeze-drying and capping, a triptolide lignocerate liposome lyophilized powder for injection was obtained.

The average particle size was 65.1 nm and the PDI was 0.087.

Example 46: Preparation of Triptolide Lignocerate Liposomes

The prescription amount of triptolide lignocerate 0.3 g, high-purity egg yolk lecithin 3 g, DSPEPEG2000 0.01 g, placed in 2 g anhydrous ethanol, heated at 55° C. to dissolve to obtain the organic phase. 50 μg of NaCl was weighed and placed in an appropriate amount of water for injection, and the aqueous phase was obtained by heating and stirring at 55° C. to dissolve it. The aqueous phase was slowly injected into the organic phase under stirring conditions, and the crude liposome was obtained by mixing. The crude liposome was extruded with extrusion membranes with pore sizes of 0.4 μm, 0.1 μm, and 0.05 μm to obtain the liposome solution. Sucrose 25 g was weighed and added to the above liposome solution. The solution was dissolved by stirring, and the solution was diluted to 100 mL with water for injection. The solution was filtered through 0.22 μm filter membrane for sterilization, dispensed, freeze-dried and capped. A a triptolide lignocerate liposome lyophilized powder for injection was obtained.

The average particle size was 81.3 nm and the PDI was 0.076.

Example 47: Preparation of Triptolide Lignocerate Liposomes

The prescription amount of triptolide lignocerate 0.2 g, high-purity egg yolk lecithin 4 g, DSPE-PEG2000 0.5 g, placed in 6 g tert-butanol, heated at 50° C. to dissolve to obtain the organic phase. An appropriate amount of water for injection was weighed and heated at 50° C. to obtain the aqueous phase. The aqueous phase was slowly injected into the organic phase under stirring conditions and mixed well to obtain the crude liposome. The crude liposome was extruded with extrusion membranes with pore sizes of 0.4 μm, 0.1 μm, and 0.05 μm to obtain the liposome solution. NaCl 60 μg, $Na_2SO_4$ 40 μg and maltose 20 g were weighed and dissolved in the above liposome solution, stirred to dissolve. The solution was diluted to 100 mL with water for injection. After passing through a 0.22 μm filter membrane for sterilization, dispensing, freeze-drying, and capping, a triptolide lignocerate liposome lyophilized powder for injection was obtained.

The average particle size was 79.1 nm, and the PDI was 0.083.

Example 48: Preparation of Triptolide Lignocerate Liposomes

The prescription amount of triptolide lignocerate 0.1 g and high-purity egg yolk lecithin 1 g were weighed and placed in 0.1 g anhydrous ethanol, and dissolved at 30° C. to obtain the organic phase. 500 μg of $Na_3PO_4$ was weighed and placed in an appropriate amount of water for injection, heated and stirred at 30° C. to dissolve to obtain an aqueous phase. The aqueous phase was slowly injected into the organic phase under stirring conditions, and the crude liposome was obtained by mixing. The crude liposomes were extruded with extrusion membranes with pore sizes of 0.4 μm, 0.1 μm, and 0.05 μm to obtain liposome solutions. Sucrose 12 g was weighed and placed in the above liposome solution, stirred to dissolve, diluted with water for injection to 100 mL. After passing through a 0.22 μm filter membrane for sterilization, dispensing, freeze-drying, and capping, a triptolide lignocerate liposome lyophilized powder for injection was obtained.

The average particle size was 63.2 nm and the PDI was 0.043.

Example 49: Preparation of Triptolide Lignocerate Liposomes

The prescription amount of triptolide lignocerate 0.4 g, high-purity egg yolk lecithin 5 g, DSPE-PEG2000 0.1 g, placed in 4 g anhydrous ethanol, heated at 55° C. to dissolve to obtain the organic phase. NaCl 10 μg was weighed and placed in an appropriate amount of water for injection, heated and stirred at 55° C. to dissolve to obtain an aqueous phase. The aqueous phase was slowly injected into the organic phase under stirring conditions, and the crude liposome was obtained by mixing. The crude liposomes were extruded with extrusion membranes with pore sizes of 0.4 μm, 0.1 μm, and 0.05 μm, respectively. The liposome liquid was collected and added with an equal amount of water for injection with the same electrolyte concentration as the above water to remove the organic solvent by ultrafiltration for 4 times to obtain the liposome solution. Sucrose 12 g and trehalose 8 g were weighed into the above liposome solution, stirred to dissolve, and diluted to 100 mL with water for injection. After passing through a 0.22 μm filter membrane for sterilization, dispensing, freeze-drying, and capping, a triptolide lignocerate liposome lyophilized powder for injection was obtained.

The average particle size was 95.5 nm, and the PDI was 0.094.

Example 50: Preparation of Liposomes of Triptolide Lignocerate

Weigh the prescribed amount of triptolide lignocerate 0.5 g, high-purity egg yolk lecithin 6 g, DSPE-PEG2000 0.4 g in 8 g of propylene glycol, and heat at 60° C. to make dissolution, get the organic phase; Weigh NaCl 50 μg in the appropriate amount of water for injection, and heat at 60° C. to make dissolution, get the aqueous phase; In the mixing conditions of the aqueous phase slowly injected into the organic phase, and then mix, that is, the crude liposome. The crude liposome was extruded by extrusion membrane with pore sizes of 0.4 μm, 0.1 μm and 0.05 μm, respectively, and the liposome liquid was collected, and an equal amount of water for injection was added and ultrafiltrated for 5 times to remove organic solvents, and the liposome solution was obtained. Weigh 15 g of sucrose into the above liposome solution, stir to make it dissolve, and use water for injection to fix the volume to 100 mL; pass through the 0.22 μm filter membrane for sterilization, dispense, freeze-dry, and cap, a triptolide lignocerate liposome lyophilized powder for injection was obtained.

The average particle size was determined to be 112.0 nm, and the PDI was 0.126.

Example 51: Preparation of Liposomes of Triptolide Lignocerate

Weigh the prescribed amount of triptolide lignocerate 0.1 g, high-purity egg yolk lecithin 1 g, DSPE-PEG2000 0.3 g in 2 g of anhydrous ethanol, and heat at 50° C. to make dissolution, get the organic phase; weigh 80 μg of NaCl, 12 g of maltose, 13 g of tremalose in the appropriate amount of water for injection, and heat at 50° C. to make dissolution, get the aqueous phase; slowly inject the aqueous phase into the organic phase under the stirring condition, and mix well, that is, the crude liposome, The crude liposome was extruded by extrusion membrane with pore sizes of 0.4 μm, 0.1 μm and 0.05 μm, respectively, and the liposome solution was collected. The liposome solution was fixed to 100 mL with water for injection; passed through 0.22 μm filter membrane to for sterilization, dispensed, freeze-dried, and capped, then a triptolide lignocerate liposome lyophilized powder for injection was obtained.

The average particle size was determined to be 75.5 nm, and the PDI was 0.087.

Example 52: Preparation of Triptolide Lignocerate Liposomes

Weigh the prescribed amount of triptolide lignocerate 0.4 g, high-purity egg yolk lecithin 5 g, DSPE-PEG2000 0.05 g in 8 g of anhydrous ethanol, and heat at 55° C. to make dissolution, get the organic phase; Weigh NaCl 60 μg in the appropriate amount of water for injection, and heat at 55° C. to make dissolution, get the aqueous phase; In the stirring condition, the aqueous phase was injected into the organic phase slowly, and mixed well, then the crude liposome was obtained. The crude liposome was extruded by extrusion membrane with pore sizes of 0.4 μm, 0.2 μm and 0.05 μm, respectively, and the liposome liquid was collected, and an equal amount of water for injection with the same electrolyte concentration was added and ultrafiltrated for 5 times to remove organic solvents, and the liposome solution was obtained. Weigh 25 g of sucrose into the above liposome solution, stir to dissolve, and then use water for injection to fix the volume to 100 mL; pass through a 0.22 μm filter membrane for sterilization, dispense, freeze-dry, and cap, then obtain a triptolide lignocerate liposome lyophilized powder for injection.

The average particle size was 96.6 nm and the PDI was 0.148.

Example 53: Preparation of Liposomes of Triptolide Lignocerate

Weigh the prescribed amount of triptolide lignocerate 0.5 g, high-purity egg yolk lecithin 5 g, DSPE-PEG2000 0.2 g, put in 5 g of anhydrous ethanol, and heat at 55° C. to make dissolution, get the organic phase; weigh NaCl 10 μg, put in the appropriate amount of water for injection, and heat at 55° C. to make dissolution, get the aqueous phase; under the condition of stirring, the aqueous phase was slowly injected into the organic phase, and mixed well, then the crude liposome was obtained. The crude liposome was extruded by extrusion membrane with pore sizes of 0.4 μm, 0.1 μm and 0.05 μm, respectively, and the liposome liquid was collected, and an equal amount of water for injection was added and ultrafiltrated for four times to remove organic solvents, and the liposome solution was obtained. Weigh 20 g of sucrose into the above liposome solution, stir to make it dissolve, and use water for injection to volume to 100 mL; pass through a 0.22 μm filter membrane for sterilisation, dispensing, freeze-drying, and capping, i.e., a triptolide lignocerate liposome lyophilized powder for injection was obtained.

The average particle size was 120.4 nm, and the PDI was 0.125.

Example 54: Preparation of Triptolide Lignocerate Liposomes

Weigh 0.3 g of the prescribed amount of triptolide lignocerate, along with 3 g of high-purity egg yolk lecithin and 0.25 g of DSPE-PEG2000, and dissolve them in 3 g of propylene glycol by heating at 45° C. to obtain the organic phase. Separately, weigh 70 μg of NaCl and dissolve it in an appropriate volume of water for injection by heating at 45° C. to prepare the aqueous phase. Under stirring conditions, gradually inject the aqueous phase into the organic phase while ensuring thorough mixing to yield crude liposomes. The resulting crude liposome was extruded through extrusion membranes with pore sizes of 0.4 μm, 0.1 μm, and 0.05 μm, respectively. The liposome liquid was collected, and the same amount of water for injection with the same electrolyte concentration as the above water was added. Ultrafiltration for 4 times was used to remove organic solvents to obtain the liposome solution. Subsequently, add 30 g of sucrose to this liposome solution and stir until fully dissolved; adjust the final volume to 100 mL using water for injection. After passing through a 0.22 μm filter membrane for sterilization, dispensing, freeze-drying, and capping, a triptolide lignocerate liposome lyophilized powder for injection was obtained.

The average particle size was 85.5 nm, and the PDI was 0.096.

Example 55: In Vivo Antitumor Effect of Triptolide Lignocerate Liposomes

Triptolide lignocerate liposomes prepared according to Examples 35, 42, and 53 were studied for their antitumor effects in a Panc 02 pancreatic cancer model, with TP (DMSO) solution and Minnelide solution as controls. The experimental design and results are outlined as follows:

1. Sample Sources

TP (DMSO) solution and Minnelide solution served as positive control drugs. TP-LA liposomes prepared in Examples 35, 42, and 53 were used as the liposome formulation.

2. Establishment of Panc 02 Pancreatic Cancer Tumor Model in Mice and Design of Drug Administration Scheme Panc 02 pancreatic cancer cells were cultured in DMEM medium at 37° C. with 5% $CO_2$. Cells were passaged every two days during logarithmic growth phase until reaching a concentration of $1\times10^7$ cells/mL. Under sterile conditions, Panc 02 cells were subcutaneously implanted into the right axilla of ICR mice to establish the pancreatic cancer model. Once the tumor volume grew to 100-300 $mm^3$, mice were randomly divided into 6 groups of 6 animals each. Groups included blank control group, TP (DMSO) solution group, Minnelide solution group, and TP-LA liposome dose groups. Drugs were administered via tail vein injection at a dose of 0.6 mg/kg (based on TP) every other day for a total of 4 doses. On the third day after the last administration, mice were euthanized. Body weights were recorded, tumors were excised and weighed, and tumor inhibition rates were calculated.

$$\text{Tumor inhibition rate} = \frac{\text{Tumor weight of blank group} - \text{Tumor weight of administered group}}{\text{Tumor weight of blank group}} \times 100\%$$

3. Antitumor Effects

Using a mouse model of pancreatic cancer, the antitumor effects of triptolide lignocerate liposomes were compared with Minnelide solution and TP (DMSO) solution. The results are presented in Table 17.

TABLE 17

Comparison of Antitumor Effects between Minnelide and Triptolide Lignocerate Liposomes

| Group | Dose (mg/kg) | Body weight change (%) | Mean tumor weight (g) | Tumor inhibition rate (%) |
|---|---|---|---|---|
| Model group | / | 16.46 | 0.698 ± 0.120 | / |
| TP solution group | 0.6 mg/kg | −7.83 | 0.417 ± 0.097 | 40.26% |
| Minnelide group | 0.85 mg/kg | 1.09 | 0.222 ± 0.029* | 68.19% |
| Example 35 | 1.18 mg/kg | 17.84 | 0.139 ± 0.043*# | 80.06% |
| Example 42 | 1.18 mg/kg | 18.02 | 0.130 ± 0.033*# | 81.38% |
| Example 53 | 1.18 mg/kg | 17.27 | 0.142 ± 0.040*# | 79.66% |

Note:
Compared with the model group,
*P < 0.05,
**P < 0.01;
compared with the TP group,
#P < 0.05,
P < 0.01.

4. Results Analysis

Figure 3:
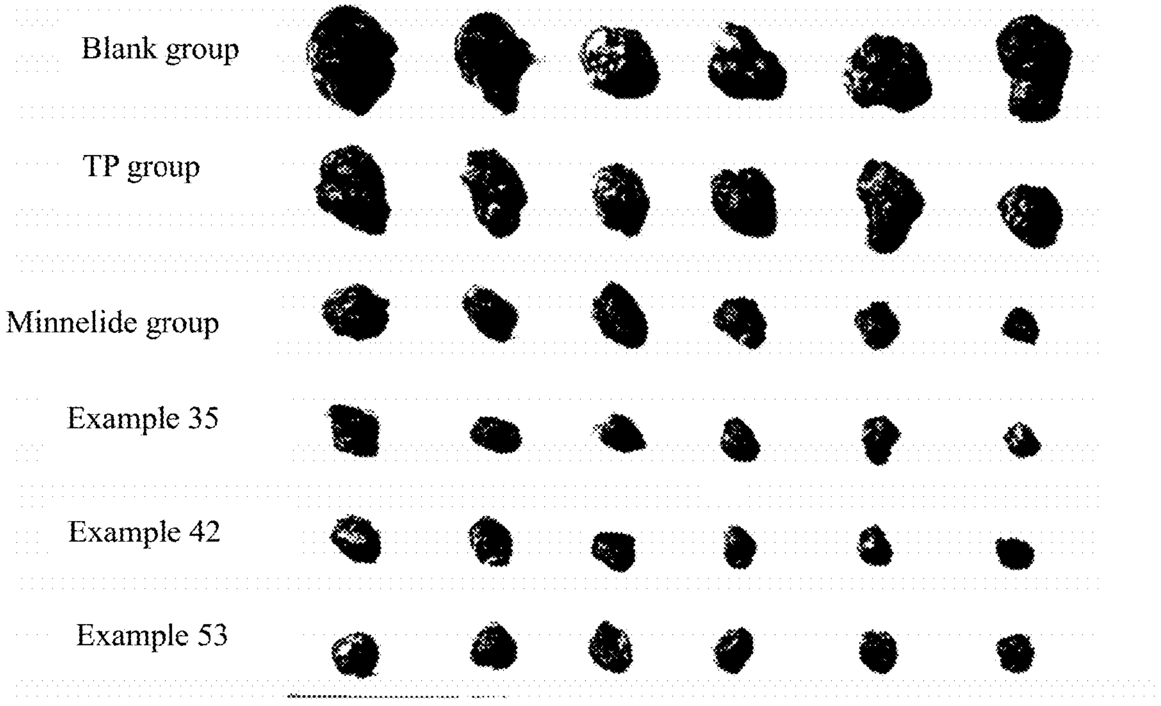
FIG. 3 shows a visualization graph of isolated tumors from each group of mice in Example 55.
Figure 4:
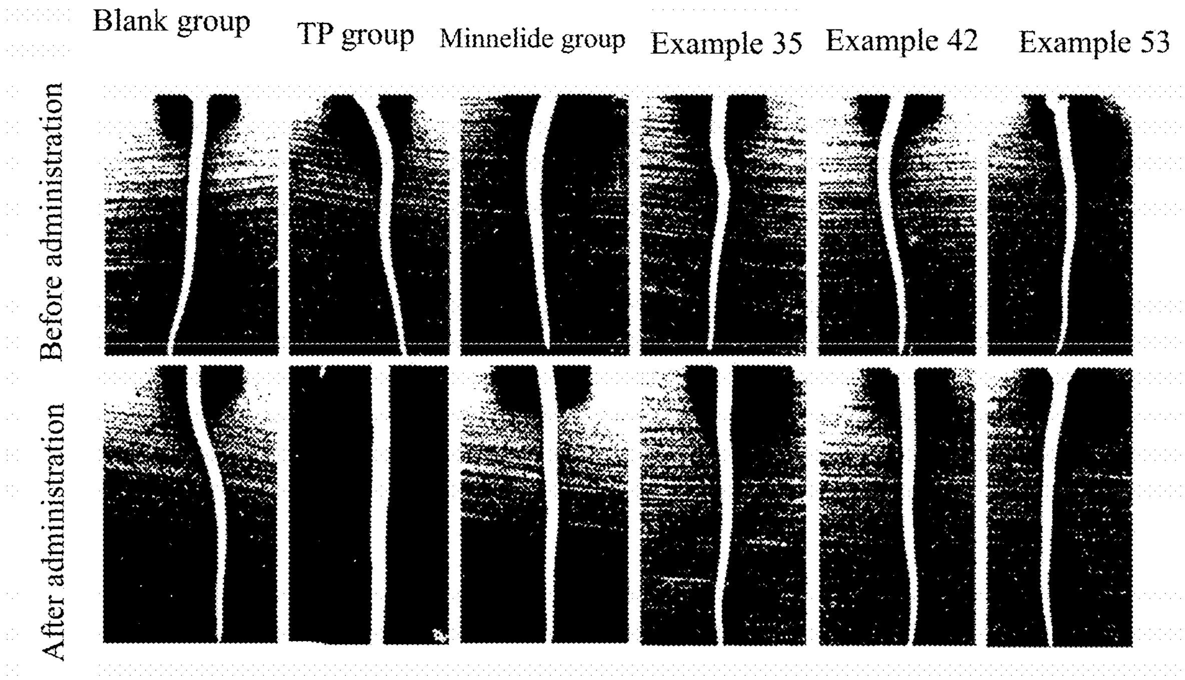
FIG. 4 shows a graph of tail vein irritability after administration of the mice in each group in Example 55.

Triptolide lignocerate (TP-LA) liposomes prepared according to Examples 35, 42, and 53 were evaluated pharmacologically in a mouse model of Panc 02 pancreatic cancer, alongside TP solution and Minnelide solution. Experimental results (see FIG. 3) demonstrated that the efficacy of TP-LA liposomes was significantly superior to TP solution and Minnelide solution. Mice administered with TP solution exhibited noticeable weight loss, while those administered with Minnelide showed considerable variability in individual body weights compared to the negative control group, indicating a distinct overall growth difference. Furthermore, mice administered with TP solution and Minnelide solution intravenously displayed varying degrees of tail swelling and ulceration, indicating significant irritation (FIG. 4). In contrast, mice treated with TP-LA liposomes showed no significant irritation, and their body weights exhibited a normal growth trend. This suggests that the liposomes prepared in this invention not only significantly enhance overall therapeutic efficacy but also improve biocompatibility.

Example 56: Liposomes of Triptolide Lignocerate for Injection Prepared in Examples 35, 42, and 53 were Selected for Irritation Evaluation 1. Irritation Protocol Design Eight rabbits (weighing 1.5-2.0 kg) were randomly divided into 6 groups. Each group received intravenous injection via the right ear vein of either saline solution, TP-LA liposomes prepared according to Examples 35, 42, and 53, TP (DMSO) solution, or Minnelide solution, at a dose of 0.22 mg/kg (calculated based on TP), administered at a rate of 1 mL/min. Simultaneously, saline of equal volume was administered via the left ear vein as a control. This procedure was repeated daily for three consecutive days.

During each day of administration, the animals' behavior and pathological changes at the injection site were observed macroscopically. Euthanasia was performed 48 hours after the last administration. Tissue samples were collected approximately 2.0 cm towards the central end from the injection site on the ear vein, fixed in 10% paraformaldehyd solution, dehydrated using an ethanol gradient, embedded in paraffin, and sectioned into slices stained with hematoxylin and ovoglobulin. All samples were examined using a BX43-DP21 light microscope (Olympus Corporation, Japan), and pathological changes were assessed.

2. Results Analysis of Irritation Evaluation

Figure 5:
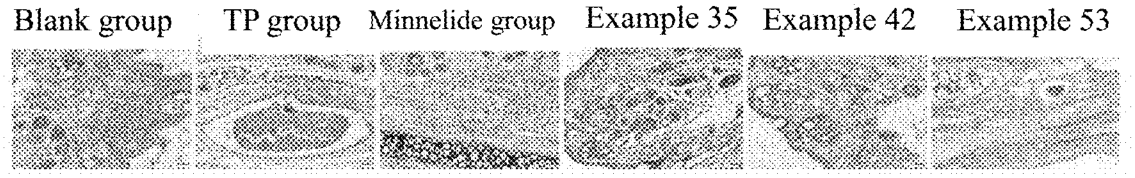
FIG. 5 shows a graph of vascular irritability in Example 56.

As shown in FIG. 5, the blank control group showed no significant congestion or bleeding along the ear vein. Vascular wall morphology was intact, and surrounding tissues exhibited no apparent inflammatory lesions. The epidermal surface of the ear skin displayed intact stratified squamous epithelial structure, with no notable alterations in subcutaneous structures such as hair follicles, sebaceous glands, or sweat glands. The central area showed normal elastic cartilage morphology, the auricular interstitial fibrous tissue had no obvious lesion, and the interstitium had a small amount of chronic inflammatory cell infiltration.

In the TP (DMSO) solution group, significant bleeding was observed along with vascular wall necrosis and notable infiltration of inflammatory cells in the surrounding tissue. Subcutaneous connective tissue appeared loose and edematous, with collagen fiber fractures and acute inflammatory cell infiltration in the ear interstitial fibrous tissue. The Minnelide solution group exhibited congestion and some instances of bleeding, with surrounding tissues showing edema and slight tissue fluid leakage.

The group treated with triptolide lignocerate liposomes for injection (Examples 35, 42, 53) showed results similar to the blank control group. Endothelial cells within the ear vein were mostly intact, with only a small amount of diffuse inflammatory cell infiltration around the vascular wall. Epidermal tissue of the skin did not exhibit significant changes such as degeneration, necrosis, or hyperplasia. In the central area, elastic cartilage morphology was normal, showing typical chondrocytes, cartilage matrix, and membrane structure.

Example 57: Preparation of Triptolide Lignocerate Liposomes

Weigh the prescribed amount of triptolide lignocerate 0.3 g and high-purity egg yolk lecithin 4 g into 5 g anhydric alcohol, heat and stir at 60° C. to dissolve and obtain organic phase; Weigh the appropriate amount of water for injection and heat it at 60° C. to obtain the aqueous phase; Under stirring condition, the aqueous phase is slowly injected into the organic phase and mixed well to obtain the crude liposome. The crude liposomes were extruded with extrusion membranes with pore sizes of 0.4 μm, 0.2 μm and 0.1 μm, respectively. The liposome liquid was collected, and the organic solvent was removed four times by ultrafiltration with the same amount of water for injection. The liposome solution was obtained; the volume of water for injection was up to 100 mL. After 0.22 μm filter membrane sterilization, dispensing, capping, namely triptolide lignocerate liposome injection.

The average particle size was 100.6 nm, and the PDI was 0.104.

Example 58: Preparation of Triptolide Lignocerate Liposomes

Weigh the prescribed amount of triptolide lignocerate 0.3 g, high-purity egg yolk lecithin 3 g, DSPE-PEG2000 0.1 g in 3 g of anhydrous ethanol, and dissolve it by heating and stirring at 55° C. to obtain the organic phase; Weigh 10 μg of NaCl in the appropriate amount of water for injection, and dissolve it by heating and stirring at 55° C. to obtain the aqueous phase. The aqueous phase was slowly injected into the organic phase under stirring conditions, and then mixed well to obtain the crude liposome; the crude liposome was extruded through the extrusion membrane with the pore sizes of 0.2 μm, 0.1 μm, 0.05 μm, and the liposome solution was obtained; the water for injection was fixed to 100 mL; sterilize through a 0.22 μm filter membrane, dispense, and cap, and obtain a triptolide lignocerate liposome injection.

The average particle size was 79.2 nm, and the PDI was 0.092.

Example 59: Preparation of Triptolide Lignocerate Liposomes

Weigh the prescribed amount of triptolide lignocerate 0.4 g, high-purity egg yolk lecithin 5 g, DSPE-PEG2000 0.1 g in 9 g of anhydrous ethanol, and dissolve it by heating and stirring at 60° C. to obtain the organic phase; weigh the appropriate amount of water for injection, and heat it at 60° C. to obtain the aqueous phase; inject the aqueous phase into the organic phase slowly under stirring conditions, and then mix it well to obtain the crude liposomes; Extrude the crude liposome with extrusion membrane of 0.4 μm, 0.2 μm and 0.1 μm pore size respectively, collect the liposome liquid, add equal amount of water for injection and ultrafiltration for 5 times to remove the organic solvent, and then obtain the liposome solution. Weigh 25 g of sucrose into the above liposome solution, stir to make it dissolve, and then use water for injection to fix the volume to 100 mL; pass through the 0.22 μm filter membrane to sterilize, dispense, freeze-dry, and cap, and then obtain a triptolide lignocerate liposome lyophilized powder for injection.

The average particle size was 108.5 nm, and the PDI was 0.147.

Example 60: Preparation of Triptolide Lignocerate Liposomes

Weigh the prescribed amount of triptolide lignocerate 0.3 g, high-purity egg yolk lecithin 3.7 g, DSPE-PEG2000 0.05 g, placed in 5 g anhydrous ethanol, heated and stirred at 55° C. to dissolve the organic phase; weigh the appropriate amount of water for injection, and heated and stirred at 55° C. to obtain the aqueous phase; the aqueous phase was slowly injected into the organic phase under the condition of stirring, and then mixed to obtain the crude liposomes. Extrude the crude liposome with the extrusion membrane with the pore size of 0.4 μm, 0.2 μm, 0.1 μm, collect the liposome liquid, add the same amount of water for injection and ultrafiltration for 4 times to remove the organic solvent, and then get the liposome solution: Weigh 20 g of sucrose to the above liposome solution, stir it to dissolve it, and then set the volume with the water for injection to 100 mL. After passing 0.22 μm filter membrane for sterilization, dispensing, freeze-drying and capping, a triptolide lignocerate liposome lyophilized powder for injection was obtained.

The average particle size was 105.5 nm, and the PDI was 0.112.

The above has been a better embodiment of the present invention has been specified, but the present invention is not limited to the said embodiment, the skilled person familiar with the field without violating the spirit of the present invention may also make all kinds of equivalent variations or substitutions, which equivalent variations or substitutions are included in the scope limited by the present application claims.

The invention claimed is:

1. A lyophilized powder comprising triptolide lignocerate, lipids, and lyoprotectant, wherein the lipids comprise all of phospholipid, cholesterol, PEG-distearoylethanolamine, and wherein liposomes are formed upon reconstitution of the lyophilized powder.

2. The lyophilized powder of claim 1, which has a weight:weight ratio of triptolide lignocerate to lipids of 1:5 to 1:30.

3. The lyophilized powder of claim 1, which has a weight:weight ratio of triptolide lignocerate to lipids of 1:10 to 1:20.

4. The lyophilized powder of claim 1, wherein the phospholipid is lecithin.

5. The lyophilized powder of claim 1, wherein the phospholipid is selected from one or more of lecithin, egg yolk lecithin, hydrogenated soybean lecithin, dipalmitoyl phosphatidylcholine, phosphatidylcholine, soy lecithin, phosphatidylserine, dimyristoyl phosphatidylcholine, distearoyl phosphatidylcholine, phosphatidylethanolamine, and sphingomyelin.

6. The lyophilized powder of claim 1, wherein the lyoprotectant is selected from one or more of trehalose, sucrose, maltose, lactose, mannitol, glucose, sorbitol, xylitol, erythritol, and threonine.

7. The lyophilized powder of claim 1, further comprising an electrolyte.

8. The lyophilized powder of claim 7, wherein the electrolyte is selected from one or more of sodium citrate, $Na_2SO_4$, NaCl, $Na_2CO_3$, $FeCl_3$ and $Na_3PO_4$.

9. A formulation made by reconstitution of the lyophilized powder of claim 1, wherein the formulation is for injection and wherein the formulation comprises liposomes comprising triptolide lignocerate.

10. The formulation of claim 9, which has a weight:weight ratio of triptolide lignocerate to lipids of 1:10 to 1:20.

11. The formulation of claim 9, which has a weight:weight ratio of triptolide lignocerate to lipids of 1:5 to 1:30.

12. The formulation of claim 9, wherein the phospholipid is lecithin.

13. The formulation of claim 9, wherein the phospholipid is selected from one or more of lecithin, egg yolk lecithin, hydrogenated soybean lecithin, dipalmitoyl phosphatidylcholine, phosphatidylcholine, soy lecithin, phosphatidylserine, dimyristoyl phosphatidylcholine, distearoyl phosphatidylcholine, phosphatidylethanolamine, and sphingomyelin.

14. The formulation of claim 9, further comprising an electrolyte.

15. The formulation of claim 14, wherein the electrolyte is selected from one or more of sodium citrate, $Na_2SO_4$, NaCl, $Na_2CO_3$, $FeCl_3$ and $Na_3PO_4$.

16. A formulation comprising liposomes comprising triptolide lignocerate and lipids, wherein the lipids comprise all of phospholipid, cholesterol, PEG-distearoylethanolamine, and wherein the formulation comprises water for injection.

17. The formulation of claim 16, which has a weight:weight ratio of triptolide lignocerate to lipids of 1:10 to 1:20.

18. The formulation of claim 16, which has a weight:weight ratio of triptolide lignocerate to lipids of 1:5 to 1:30.

19. The formulation of claim 16, wherein the phospholipid is lecithin.

20. The formulation of claim 16, wherein the phospholipid is selected from one or more of lecithin, egg yolk lecithin, hydrogenated soybean lecithin, dipalmitoyl phosphatidylcholine, phosphatidylcholine, soy lecithin, phosphatidylserine, dimyristoyl phosphatidylcholine, distearoyl phosphatidylcholine, phosphatidylethanolamine, and sphingomyelin.

21. The formulation of claim 16, further comprising an electrolyte.

22. The formulation of claim 21, wherein the electrolyte is selected from one or more of sodium citrate, $Na_2SO_4$, NaCl, $Na_2CO_3$, $FeCl_3$ and $Na_3PO_4$.

* * * * *